United States Patent [19]

Diamond et al.

[11] Patent Number: 4,766,062

[45] Date of Patent: * Aug. 23, 1988

[54] DISPLACEMENT POLYNUCLEOTIDE ASSAY METHOD AND POLYNUCLEOTIDE COMPLEX REAGENT THEREFOR

[75] Inventors: Steven E. Diamond, Springfield; Joseph G. Brewen, Convent Station; Jon I. Williams, Montclair; Marian S. Ellwood, Summit, all of N.J.; Mary Collins, Watertown; Edward F. Fritsch, Concord, both of Mass.

[73] Assignees: Allied Corporation, Morristown, N.J.; Genetics Institute, Inc., Cambridge, Mass.

[*] Notice: The portion of the term of this patent subsequent to Jun. 23, 2005 has been disclaimed.

[21] Appl. No.: 607,885

[22] Filed: May 7, 1984

[51] Int. Cl.$^4$ .................. C12Q 1/68; G01N 33/566
[52] U.S. Cl. .................................... 435/6; 435/803; 435/810; 935/78; 436/501
[58] Field of Search .............. 935/3, 6, 9, 10, 76, 935/77, 78; 436/94, 501, 518, 538, 541, 542; 536/27; 435/6, 803, 810

[56] References Cited

U.S. PATENT DOCUMENTS

| | | | |
|---|---|---|---|
| 4,205,952 | 6/1980 | Cais | 436/518 |
| 4,358,535 | 11/1982 | Falkow et al. | 435/5 |
| 4,388,295 | 6/1983 | Cocola et al. | 424/1 |
| 4,395,486 | 7/1983 | Wilson et al. | 435/6 |
| 4,434,236 | 2/1984 | Freytag | 436/512 |
| 4,486,539 | 12/1984 | Ranki et al. | 436/504 |
| 4,568,649 | 2/1987 | Bertoglio-Matte | 436/534 |
| 4,629,689 | 12/1986 | Diamond et al. | 436/501 X |

FOREIGN PATENT DOCUMENTS

| | | |
|---|---|---|
| 0063879 | 11/1982 | European Pat. Off. |
| 0070687 | 1/1983 | European Pat. Off. |
| 0097373 | 1/1984 | European Pat. Off. |
| 0124221 | 11/1984 | European Pat. Off. |
| 127327 | 12/1984 | European Pat. Off. |
| 0133288 | 2/1985 | European Pat. Off. |
| 0139489 | 5/1985 | European Pat. Off. |
| WO83/01459 | 4/1983 | PCT Int'l Appl. |
| WO83/02277 | 7/1983 | PCT Int'l Appl. |
| WO84/02721 | 7/1984 | PCT Int'l Appl. |
| 2125964A | 3/1984 | United Kingdom |

OTHER PUBLICATIONS

Langer, P. R. et al., *Proc. Nat'l. Acad. Sci. USA*, vol. 78, No. 11, 1981, pp. 6633–6637.
Wu, A. M. et al., *Cell*, vol. 30,. Aug. 1982, pp. 37–44.
C. Green & C. Tibbetts, "Reassociation Rate Limited Displacement of DNA Strands by Branch Migration," Nucleics Acids Research, vol. 9, No. 8, pp. 1905–1918 (1981).
J. Lesely Woodhead, et al., "Non-Radioactive Gene-Specific Probes", Biochemical Society Transaction, p. 279, vol. 12, 1984.
N. Small, et al., "The Properties of Immobilized Horseradish Peroxidase", Biochemical Society Transaction, p. 280, vol. 12, 1984.

*Primary Examiner*—Charles F. Warren
*Assistant Examiner*—Jeremy M. Jay
*Attorney, Agent, or Firm*—Alan M. Doernberg

[57] ABSTRACT

A diagnostic reagent is disclosed containing a complex of a probe polynucleotide (P) bound via purine/pyrimidine hydrogen bonding to a labeled polynucleotide (L). The probe (P) contains a target binding region (TBR) capable of binding to a target nucleotide sequence (G) of a biological sample. A method is disclosed in which contact with a sample containing the target nucleotide sequence (G) causes binding, initially between G and a single-stranded portion (IBR) of the target binding region (TBR). Thereafter the labeled polynucleotide (L) is displaced from the complex by branch migration of (G) into the (P)/(L) binding region. Determination of displaced labeled polynucleotide (L) gives a value which is a function of the presence and concentration of target nucleotide sequence (G) in the sample.

49 Claims, 5 Drawing Sheets

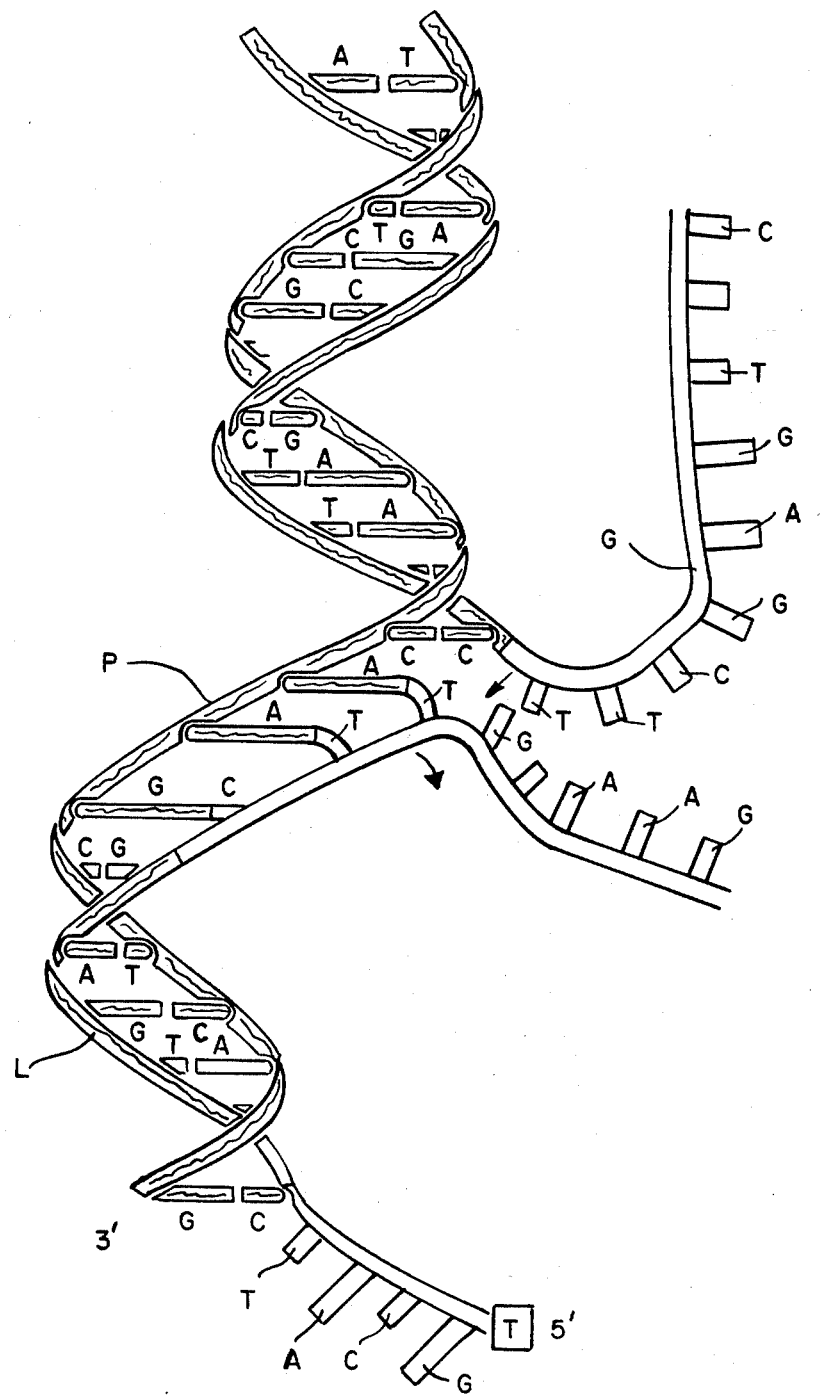
FIG.ID

DISPLACEMENT POLYNUCLEOTIDE ASSAY METHOD AND POLYNUCLEOTIDE COMPLEX REAGENT THEREFOR

BACKGROUND OF THE INVENTION

The present invention relates to a diagnostic assay method for detecting the presence of a target nucleotide sequence (either DNA or RNA) in a biological sample, and to a polynucleotide reagent complex therefor.

Conventional methods for detecting the presence of a particular polynucleotide in a biological sample typically involve immobilization of nucleic acid of the sample on a surface as the initial step. Once the sample is immobilized, a probe polynucleotide strand, tagged usually with a detectable label such as radioactive phosphorus atoms, is incubated with the immobilized sample so as to bind to the immobilized sample by purine-/pyrimidine base sequence-specific complementary base pairing when the immobilized sample contains the target nucleotide sequence. After washing off the labeled probe which has not so hybridized, the presence or absence of label on the support is then determined. Techniques for this determination include exposure of a photographic film, liquid scintillation counting, and fluorescence microscopy.

Ward and coworkers (see EPA No. 63,879 (1982)) have described a variation of this technique in which, rather than tagging the probe directly with a detectable label, the probe is tagged with a nonisotopic substituent such as biotin on certain nucleotides. In such case, after the unhybridized probe is washed off, the support is contacted with a reagent such as avidin linked to an enzyme. The avidin-enzyme complex binds selectively to biotin because of the high avidin-biotin binding affinity, so as to affix enzyme selectively where the target nucleotide sequence has been immobilized on the substrate. Thereafter, a substrate for the enzyme is added and products of the enzymatic reaction are detected, yielding an amplified signal functionally dependent upon the initial concentration of target nucleotide sequence on the substrate. See also EPA No. 97,373 of ENZO BIOCHEM, INC (Jan. 4, 1984).

A variation in the above nonisotopic system has also been described in another European patent application of Standard Oil of Illinois (EPA No. 70,687 (1983)) in which, in one form (see pages 8–10 thereof), two probes specific for the target nucleotide sequence are employed. The first probe, which can hybridize to a first portion of the target nucleotide sequence, is affixed to a solid support such that, upon incubation of the solid support with a sample of the biological material, target nucleotide sequences in the sample will bind to the support selectively via this first immobilized probe. Thereafter, the second probe, which can hybridize selectively to a second and distinct portion of the target nucleotide sequence, is used to contact the support. Again, if the target nucleotide sequence had been present in the biological sample, the second probe will now bind selectively to that nucleotide sequence; and a combination structure (or sandwich) will be created linking the second probe to the support via the first probe and the target nucleotide sequence. The reference discloses labeling this second probe with a moiety directly or indirectly generating or absorbing specific wavelengths of light (e.g., a fluorescent label, a phosphorescent label or a chemiluminescent label). By separating the support from unbound solution constituents at each stage, the presence of label in the phase with support after the third separation will be a function of the presence and concentration of the target nucleotide sequence in the sample. See also WO No. 83/01459 of Orion-Yhtma Oy (Apr. 29, 1983).

A different diagnostic method for a specific target nucleotide involving digestion of double-stranded sample nucleic acid in solution with a restriction enzyme, followed by detection of specifically sized fragments on filter paper, is disclosed in U.S. Pat. No. 4,395,486 to Wilson et al. In that disclosure, the presence of the single base substitution causative of sickle cell anemia abolishes a specific site for restriction enzyme cleavage, and thereafter two specifically sized small fragments which are usually detected are then detected in reduced amounts (for sickle cell trait) or cease to be detected (for sickle cell anemia).

While the above procedures will detect the presence of nucleotide sequences in biological samples in many cases, they each have the disadvantage of either multiple steps or steps with necessarily long incubation periods that make them impracticable for easy use in a clinical laboratory. Furthermore, many of these processes suffer from a limited selectivity or sensitivity with regard to interfering polynucleotide sequences or the detection of low levels of target nucleotide sequence reliably against the background signal. In particular, nonspecific binding of the labeled probe represents a source of substantial background signal in each process.

Apart from the analysis of biological samples for target nucleotide sequences, various aspects of the physical chemistry of hybridization (formation of double-stranded helices between complementary polynucleotide sequences) have been studied. These studies have included examination of the phenomena of strand migration and displacement in nucleic acid, both in vivo and in vitro. By referring to such studies, however, we do not admit that the phenomena of strand migration and displacement have any obvious applicability to diagnosis and detection. C. Green and C. Tibbetts, *Nucleic Acids Research* vol. 9, No. 8, pp. 1905–18 (1981), have described the formation of a complex (hybrid) of a 6.1 kb (6100 base long) single-stranded DNA polynucleotide hybridized near its middle (the interval 1.7–3.3 kb) by an end-labeled complementary DNA polynucleotide of 1.6 kb length. Addition to this complex, in solution, of the 6.1 kb complementary strand caused rapid displacement of the labeled polynucleotide (see FIG. 2 on page 1910 of this reference), monitored by taking aliquots of the reaction mixture, separating by gel chromatography and analyzing by autoradiography. The displaced 1.6 kb polynucleotide increased steadily from under 10% to over 90% of the radioactive signal in a period of more than 85 minutes (depending upon concentration) with the 1.6/6.1 kb hybrid accounting for the bulk of the remaining radioactivity. The presumed partially displaced intermediate, which would have a total mass equivalent to 13.8 kb of DNA (both long strands and a partially displaced short strand) was apparently not detected. The authors concluded that the initial hybridization of the two 6.1 kb polynucleotides, forming a branched species, was the rate-limiting step; and that displacement along the 1.6 kb paired region of a labeled polynucleotide was very rapid, consistent with a calculated average lifetime of the branched (13.8 kb mass equivalent) species of 0.8 minutes. They indicate the possibility of both single-branched or doubly nucleated (D-looped) intermediate species (illustrated on page 1912 of the reference). In order to better study the phenomenon of branch migration, they attempted to slow the displacement process, by using drugs which might retard the migration phenomenon and/or by using complexes with more than 1.6 kb of hybrid base pairing (see pages 1931–1914 of the reference). It should be noted that the 1.6/6.1 kb species was challenged by Green et al only with the 6.1 kb complement, purified away from any non-specific strands.

BRIEF DESCRIPTION OF THE INVENTION

The present invention is based upon the rapid displacement of a labeled polynucleotide from a probe polynucleotide by the target nucleotide sequence of a sample, enabling direct or indirect measurement of label found in or on the displaced labeled polynucleotide (or in some cases the labeled polynucleotide not displaced). This label serves as a reliable and quantitative measurement functionally related to the presence and concentration of target nucleotide sequence in a sample. Accordingly, the present invention includes a method for determining the presence of a predetermined target nucleotide sequence (either DNA or RNA) in the nucleic acid of a biological sample which comprises the steps:

(a) providing a reagent complex of (i) a probe polynucleotide which is capable of base pair binding via hydrogen bonds of purine/pyrimidine base pairs to the target nucleotide sequence, and (ii) a labeled polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the target nucleotide sequence;

(b) contacting the reagent complex with a sample under conditions in which the target nucleotide sequence, if present, binds to the probe polynucleotide and displaces labeled polynucleotide from the reagent complex; and (c) determining the presence (which includes of course determining the amount) either of labeled polynucleotide displaced from the reagent complex or of the labeled polynucleotide remaining in the reagent complex.

The present invention also includes a diagnostic reagent for determining the presence of a target nucleotide sequence in the nucleic acid of a biological sample comprising the reagent complex of:

(i) a probe polynucleotide which is capable of binding via hydrogen bonds of purine/pyrimidine base pairs to the target nucleotide sequence, and (ii) a labeled polynucleotide which is bound via hydrogen bonds of purine/pyrimidine base pairs to the probe polynucleotide in a region of the probe polynucleotide at least partially coextensive with the region in which the probe polynucleotide is capable of binding to the target nucleotide sequence;

the base pairing between the target nucleotide sequence and the probe polynucleotide being of sufficient cumulative binding strength (as defined below) for the target nucleotide sequence, if present in a sample with which the reagent is contacted, to be able to displace labeled polynucleotide from the reagent complex.

BRIEF DESCRIPTION OF THE FIGURES

FIG. 1D is an enlarged view similar to FIG. 1C, in which the helical structure of double-stranded portions is schematically shown;

DETAILED DESCRIPTION OF THE INVENTION

Figure 1A:
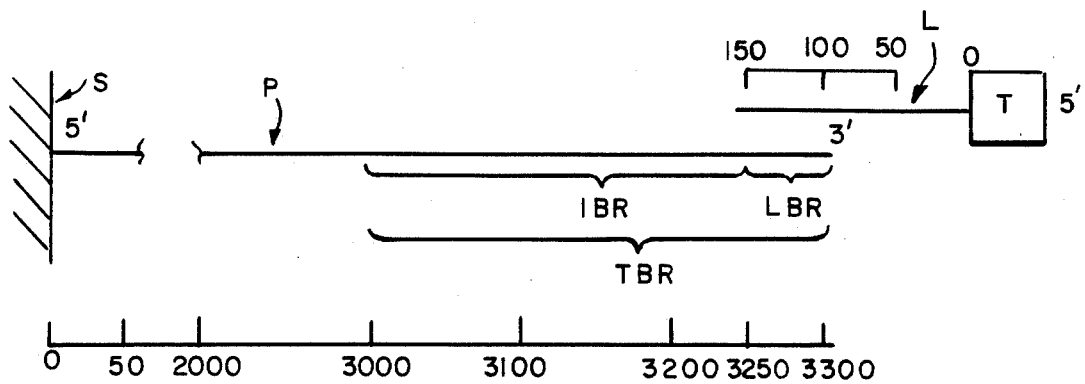
FIG. 1A is a schematic view of one embodiment of the reagent complex of the present reagent useful in the present process.

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3',5'-phosphodiester linkages, and linked by carbon-nitrogen bonds at the 1-carbon of the sugar to pendant purine or pyrimidine bases such as, but not limited to, uracil (linked naturally to ribose only as rU), thymine (linked naturally to deoxyribose only as dT), cytosine (dC or rC), adenine (dA or rA) and guanine (dG or rG). Polynucleotides thus include strands of deoxyribonucleic acid (DNA) and strands of ribonucleic acid (RNA).

The ends of such Polynucleotide Strands are referred to as the Five Prime (5') end, where the 5-carbon of the pentose is not linked to another pentose (but may bear hydroxyl, monophosphate or other natural or synthetic moieties), and the Three Prime (3') end, where the 3-carbon of the pentose is not linked to another pentose (but may similarly bear hydroxyl, monophosphate or other natural or synthetic moieties).

Complementary Base Pairing or Purine/Pyrimidine Base Pairing refers to the hydrogen bonding between opposite bases pendant on two antiparallel Polynucleotide Strands, which is most energetically favorable for natural DNA when dG is opposite dC and dA is opposite dT. Bases other than the five naturally-prevalent ones also have preferential pairing: for example, 5-methylcytosine binds preferentially to guanine. For illustrative purposes, this pairing is shown in many of the Figures by parallel straight lines with apposite strands directed in antiparallel directions (in the 5' to 3' sense). It should be appreciated, however, that the actual geometry of double-stranded segments will normally be helical (the well-known double helix) of various pitches, as schematically illustrated in FIG. 1D.

Hybridization is used herein to refer to admixing two Polynucleotides under conditions conducive to the formation of double-stranded structures, with Complementary Base Pairing causing such double stranded structures to form where complementary sequences or nearly complementary sequences are present.

The basic components of the method of the invention are a probe polynucleotide (sometimes called herein the probe), a labeled polynucleotide (sometimes called herein tagged polynucleotide or release tag), and the biological sample containing nucleic acid, a portion of which is sometimes called herein the target polynucleotide or target nucleotide sequence. A sample may or may not contain a target nucleotide sequence. In some cases a support is also provided, either to which the reagent complex is immobilized via the probe (such that the probe is sometimes called an immobilized probe or immobilized probe polynucleotide), or in other cases as a part of the separation step that may follow displacement as a part of the determination step. In practicing the process, additional reagents or equipment are frequently required for readout; the term readout refers to the direct or indirect detection of labeled polynucleotide in one or more phases of (usually separated) reaction materials, and especially in a liquid phase by virtue of displacement from the reagent complex and separation of displaced labeled polynucleotide in solution from probe polynucleotides and reagent complexes.

In the practice of the present invention, the probe polynucleotide can be a linear or circular polynucleotide capable of binding specifically through complementary base pairing in at least one region of its purine/pyrimidine base sequence to specific target nucleotide sequences of a sample. This binding may be between DNA and RNA, between DNA and DNA or between RNA and RNA. Accordingly, the probe may either be DNA or RNA. As discussed more fully below, it is generally only a specific region of the probe which binds selectively to the target nucleotide sequence. Other regions of the probe may be of various naturally occurring or synthesized sequences which do not participate in the hybridization reaction, but which may play an important role in the present invention, e.g., by serving as a site for attachment to a support or by providing some degree of separation between the support and the region to which the target nucleotide sequence binds, if desired.

Referring to the region of the probe to which the target nucleotide will specifically bind, called herein the target binding region (TBR in the Figures), the binding may be perfect, in the sense that each nucleotide in the sequence finds its correct complementary binding partner (e.g., dA to dT) in the target nucleotide sequence or may contain some mismatches. At least one portion of the target binding region of the probe is preferably single-stranded in the reagent complex, i.e., it is not complementary to labeled polynucleotide sequences; this single-stranded region is sometimes called herein the initial binding region (IBR in the Figures) because the target nucleotide sequence can bind to this region of bases without displacing any of the labeled polynucleotide. Such initial binding region of the probe is at least fifteen bases in length, and is preferably at least fifty bases in length. The overall target binding region includes the initial binding region and most or (preferably) all of the labeled polynucleotide binding region (LBR in the Figures and discussed below). The length of the overall target binding region is not independently critical, but rather can be considered as a function or sum of the preferred or more preferred lengths of the IBR and LBR portions. Base lengths of the initial binding region of the probe above five hundred are generally not required, but are not significantly disadvantageous in most cases. A suitable lower limit on the length of this region of base pairing for clinical laboratory applications is somewhat dependent upon base sequence of the target binding region of the probe polynucleotide and base composition and other physical factors described below, and especially upon the conditions for intended hybridization, mode of attachment, if any, of the probe to a support, kinetics of hybridization and the readout system employed.

The solid phase to or on which the probe is immobilized in certain embodiments may be of almost any conventional type, including especially polymeric materials, ceramic materials, walls of a test tube or other container, paper, nitrocellulose or glass. In some forms of the invention, the solid phase consists of particles or beads made of materials such as protein, polystyrene, latex or glass.

The means of attachment of the probe to the solid support may be simple adsorption, but is preferably some form of specific covalent linkage, ionic bonding or hydrogen bonding. In the case of covalent linkage, the binding may be direct as by reaction between chemical moieties on the surface of the support (for example, amine or carboxyl moieties) and moieties on the polynucleotide, and especially hydroxyl or phosphate moieties on the end sugar rings of the polynucleotide. Linking agents which are specific to the free secondary hydroxyl normally present at the 3' end include phosphites, succinic anhydride and phthalamide. Linking agents which are specific to the phosphate normally present on the sugar at the 5' end (at least for most naturally occurring polynucleotides or products of most cleavage reactions) include carbodiimides such as 1-ethyl-3,3-dimethylaminopropylcarbodiimide, with or without imidazole or 1-methylimidazole. See B. C. F. Chu et al., *Nucleic Acids Research* Vol. 11, No. 8, pp. 6513-29 (1983). Such linkages which are specific to an end or other small portion of the probe, if remote from the target binding region, can permit greater degrees of freedom during the hybridization reaction compared to adsorption or other similar physical or non-specific chemical means of attachment. With such greater degrees of freedom, the minimum length of the target binding region or minimum time for the hybridization can be lowered.

Non-specific covalent linkages include linkages between the substrate and free bases along the chain via moieties such as m-aminobenzyloxy methyl (ABM), m-diazobenzyloxy methyl (DBM) or o-aminophenylthioether (APT). See H. Bunemann et al., *Nucleic Acids Research* Vol. 10, No. 22, pp. 7163–7169 (1982) (two articles). Other exemplary non-specific linking chemistry is described in U.S. Pat. No. 4,286,964 to B. Seed (1981).

In addition to direct covalent linkage, the probe polynucleotide may be indirectly linked to the support by a linking or spacer molecule. Examples of indirect covalent linking reagents include spacer reagents which can react by carbodiimide chemistries both with functional groups (for example, esters) on the support and with the phosphate normally present on the 5' terminal sugar of the polynucleotide. Such spacer molecules include the aliphatic diamines used in the above-cited Chu et al. article which, once attached to the terminal phosphate, can then be linked to active groups on the support such as N-hydroxysuccinimide esters. Other spacer molecules include hydroxyalkanoic acids.

Other spacer molecules can contain a functional moiety such as phenyl ketone which will react directly with a support having hydrazine moieties, forming a resulant hydrazone.

The probe further may be noncovalently linked to the support by interaction of some portion of the probe with affinity reagents that are adsorbed or covalently bound to the support. Examples include (1) immobilization of a short single-stranded polynucleotide on the support which can hybridize to some portion of the probe polynucleotide not coextensive with the region in the probe which is capable of binding to the target nucleotide sequence and (2) binding of a chemically modified probe polynucleotide carrying one or more avidin or biotin moieties to a support having biotin or avidin moieties, respectively, adsorbed or covalently bound to the support. The latter method is based on the high affinity ($K_{diss}$ approximately $10^{-15}M$) of the small molecule biotin for the protein avidin (or strepavidin).

While the present invention is not limited with regard to the spacings between the point or points of attachment of the probe to a support and the region of the probe polynucleotide which binds specifically to the target nucleotide sequence, it is preferable that this spacing be sufficiently large for the hybridization between target nucleotide sequence and target binding region of the polynucleotide to occur such that the target binding region of the probe has maximal freedom of movement during hybridization.

In other embodiments of the invention, the probe polynucleotide is not immobilized to a support in the complex, but rather the entire reagent complex is in solution as the reagent is mixed with a biological sample such that hybridization will occur, if at all, in solution. In some of those solution hybridization embodiments, the probe does contain a substituent (such as an affinity reagent, e.g., biotin, or a chemical moiety, e.g., a chemical hapten such as dinitrophenol) so as to be immobilizable or separable if desired after hybridization, e.g., by passing through a porous bed or filter with strepavidin on a support. Such immobilization will cause only displaced labeled polynucleotides to remain in the liquid phase, for subsequent determination. Still other forms of the invention involving solution hybridization include other forms of separations: size exclusion chromatography (see Example 1, below), electrophoresis (see, e.g., Examples 2–4, below), or other physical separation techniques. Additional forms of the invention, described more fully below in connection with read-out, involve determination of displaced labeled polynucleotide without any separation from complex. Of course many of such determinations without separation apply equally to processes wherein the complex includes an immobilized probe polynucleotide.

Such probe polynucleotides can be manufactured reproducibly in a variety of ways, e.g., cloned in or as a part of a suitable plasmid or viral vector isolated from a bacterium or other suitable microorganism, as a part of the genetic material of a microbe or obtained from any other pertinent biological source. Generally, only a small region of nucleic acid that includes a probe polynucleotide sequence (a portion of which forms the target binding region) will be inserted into any such cloning vectors by recombinant techniques; the remainder, if any, of the cloned insert that is not probe polynucleotide sequence can conveniently be chosen from any polynucleotide sequence heterologous to the target nucleotide sequence. In certain embodiments of this invention, such heterologous sequences can include sequences deliberately selected for specific properties such as the presence of a unique restriction enzyme recognition site. Under some conditions an entire gene or a sequence including an entire gene may be used as an insert, with the vector plus inserted nucleotide sequence either in circular or linear form. In the event that the probe polynucleotide is double-stranded when manufactured, denaturation (either thermally, by adjustment of pH or by disruption of base pairing with other conventional techniques) will normally follow isolation. Cleavage (especially by restriction enzymes or by site-specific chemical cleavage) will normally be used to form double-stranded segments of desired linear form and, if double-stranded circular forms are grown, will precede denaturation. In some cases it may be preferred to purify individual strands from a double-stranded structure to be used individually as probe polynucleotides (or one as a probe polynucleotide and one as a labeled polynucleotide). This purification can be done by standard techniques such as denaturing gel electrophoresis or affinity chromatography. In some instances, the probe polynucleotide is produced as a single-stranded molecule by replication using single-stranded vectors such as M13 bacteriophage. In some other instances, as described below, the labeled polynucleotide can be manufactured in the same molecule.

The labeled polynucleotide used in the present method and reagent is generally a smaller piece of either DNA or RNA than the probe polynucleotide and has two features of significance: (a) stable but reversible binding to the probe at a specific locus and (b) a label susceptible to detection, especially after displacement. These features are discussed herein separately, followed by consideration of the effect certain types of labeling have on stability and displacement.

The pairing between the labeled polynucleotide and the probe polynucleotide will generally occur over a smaller number of bases than the pairing between the target nucleotide sequence and the probe. In most cases, the bases of the probe polynucleotide to which the labeled polynucleotide specifically binds are a subset of the bases of the probe later binding to the sample nucleotide sequence, and thus represent a portion of what is called above the target binding region of the probe.

The term labeled polynucleotide binding region (LBR) is used herein to refer to that sequence of bases in the probe to which the labeled polynucleotide is bound in the complex. In preferred embodiments (as illustrated by all Figures except FIG. 1G) the labeled polynucleotide binding region is totally part of the target binding region (see especially FIG. 1A); in other embodiments (see FIG. 1G) only a portion (but preferably the major portion) of the labeled polynucleotide binding region is a part of the target binding region. Lengths of labeled polynucleotide binding region outside the target nucleotide binding region of the probe polynucleotide region that are greater than about 15 bases are not preferred because of the potential difficulty of disassociating the labeled polynucleotide from the probe once the only attachment is via pairing in this region. In some of the preferred embodiments, the region of the probe polynucleotide to which the labeled polynucleotide binds is a subset at or near one end of the larger region of the probe polynucleotide to which the target nucleotide sequence of the sample subsequently binds. In some such embodiments, if the probe is immobilized in the complex, the aforementioned one end of the larger region is at or near an end of a linear probe polynucleotide (as illustrated in FIG. 1A and discussed below; note, however, that the other end of the TBR may also be used as an LBR).

Figure 6:
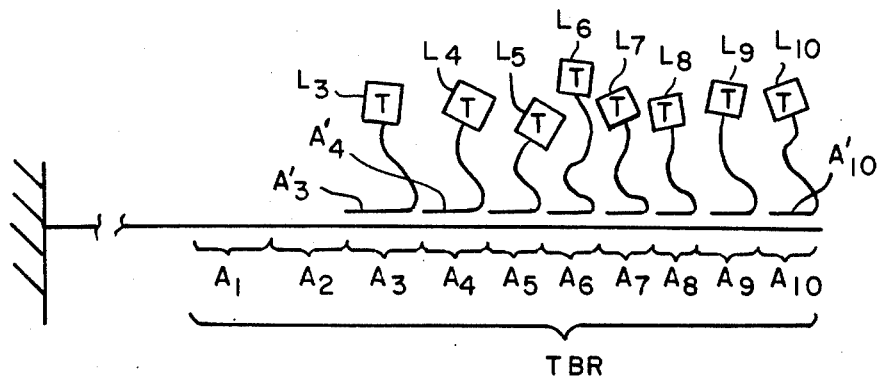
FIG. 6 is a view similar to FIG. 1A of a reagent complex according to a seventh embodiment of the present invention.

The present reference to a labeled polynucleotide and a probe polynucleotide as distinct entities should not be understood, however, to be a requirement that they are linked solely by base-pairing or that there is necessarily only one labeled polynucleotide attached to each probe polynucleotide or that there is only one labeling moiety (tag) per labeled polynucleotide. Other forms of attachment of probe to labeled polynuclotide may also be present, but are generally not preferred. In embodiments without a separation, severing such other attachment of probe to labeled polynucleotide may or may not be required, depending upon whether or not displaced labeled polynucleotides still attached by such other means appear in the detection method as if they were totally displaced. Severing such other attachment before, during or after displacement but, in any event, before the determination step is preferred. Multiple labeled polynucleotides on a single probe strand (as illustrated in FIG. 6 and described below) is a form of the invention which may have special application when greater numbers of displaced tags per displacement event are desired.

The size of the labeled polynucleotide binding region of the probe is not itself critical to the present invention, because wide variations in this size can be compensated for, e.g., by modifying the temperature of the displacement step (contacting step (b) described above) and the size of the region of the probe to which the sample binds. A generally preferred size for labeled polynucleotide binding region (and the corresponding base sequence of the labeled polynucleotide) is at least about 15 bases, preferably at least 20 bases, more preferably at least about 25 bases. A preferred range is about 20 to about 500 bases (with up to 1000 bases being also preferred), especially about 25 to about 200 bases. Labeled polynucleotides with unusually short pairing segments (giving regard to factors such as GC content) will dissociate from the probe in a non-specific manner if the temperature of the displacement step is too high (also giving consideration to factors such as salt concentration which affect melting temperatures). See D. Freifelder et al, *Biopolymers*, vol. 7, pp. 81–93 (1969). There is no essential advantage in unusually long pairing segments (e.g., over 1000 bases). Such long pairing segments are sometimes less preferred because the overall target nucleotide region of the probe could then become longer and require necessarily longer target nucleotide sequences for successful displacement of the labeled polynucleotide. The binding portion of the labeled polynucleotide may, if too long, no longer easily be manufactured by certain techniques available or best suited for small polynucleotides: e.g., organic chemical synthesis of the entire labeled polynucleotide. Organic chemical synthesis is generally easier at present for labeled polynucleotide binding regions of less than about 100, and especially less than about 60; however, improvements in such synthetic techniques could make longer sequences easy to make as well.

The minimum length of labeled polynucleotide (and also of labeled polynucleotide binding region) is related primarily to reagent complex stability. Factors other than length which affect this stability include GC content (whose effect on melting temperature is well known) and internal mismatches. Melting temperature is a useful way to establish an effective length for sequences having one or more internal base pair mismatches. As an example, a sequence of 30 bases having one internal mismatch (and thus only 29 exact pairs) may perform (at least with regard to reagent complex stability) effectively like a shorter exactly matched sequence; the degree of departure from behavior as 29 base pairs will depend upon the position of any base pair mismatches and the base change that has been made. Effective length can be expected to differ depending upon whether the mismatched pair is purine/purine, purine/pyrimidine or pyrimidine/pyrimidine. Any effective length can be empirically determined, however, by melting temperature experiments in which a series of probe/labeled polynucleotide complexes are subjected to various temperature regimes as illustrated in Example 8, below, and in articles such as R. L. Ornstein and J. R. Fresco, *Biopolymers*, Vol. 22, pp. 1979–2000 (1983). By determining a melting temperature of a complex of probe with a labeled polynucleotide containing mismatches, and comparing that value with melting temperatures of complexes with slightly shorter lengths of pairing (but perfect matching within the paired region) on the same probe polynucleotide, the effective pairing length of the labeled polynucleotide with mismatches can be estimated and applied to the above preferred and more preferred ranges. The above correlations based upon melting points are intended, however, primarily as an easy estimation tool. The actual degree of preference for a given labeled polynucleotide binding region is based in part upon how well the labeled polynucleotide actually stays in the complex during storage of the reagent or contact with non-homologous nucleic acids under use conditions (but is still displaced by nucleic acids with the target nucleotide sequence). While mismatches are permitted, they are in general not preferred and, when present, generally comprise no more than two fifths and preferably comprise no more than one tenth of the region of pairing (e.g., a maximum of three mismatches and twenty-seven perfect matches in a 30 base pair long region of labeled polynucleotide/probe polynucleotide pairing).

The labeled polynucleotide may contain regions of nucleotides, in addition to the pairing region, which do not specifically bind to the probe polynucleotide. Such regions may serve to link the pairing region to the tag, may themselves be tagged (e.g., by radioactive labeling or by covalent attachment to an indirect marker such as avidin or biotin) or merely be present without any particular function. The labeled polynucleotide may itself be linear or circular and may be (but is preferably not) double stranded in regions other than the pairing region. By analogy to Example 5, below, the labeled polynucleotide is preferably not circular when the probe polynucleotide is circular.

One or more tags may be located (using conventional techniques) generally at one of several points along the labeled polynucleotide (especially if the tag is radioactivity or biotin or the like), only at one end or only at one specific internal location (e.g., to a purine or pyrimidine base not involved in base pairing to the probe polynucleotide). Provided that there is at least one region of the labeled polynucleotide unpaired in the reagent complex, the tag is preferably present or concentrated on or within such unpaired region. Directly detectable tags which may be used include radioactivity (especially phosphorus-32, sulfur-35, carbon-14 or iodine-125 labeled nucleotides), fluorescence (such as fluorescein or rhodamine derivatives attached to the free end of a labeled polynucleotide or to one or more of the unpaired bases of a labeled polynucleotide) or moieties detectable by other means (including being cleaved off) such as the haptenic moiety dinitrophenol. Indirectly detectable tags include those modifications that can serve as antigenic determinants, affinity reagents, antigens or antibodies recognizable through immunochemical or other affinity reactions such as described in EPA No. 63,879, WO No. 83/02277 and EPA No. 97,373, referenced above and exemplified by biotinated nucleotides present in or added onto the labeled polynucleotide (such as by the enzyme terminal deoxynucleotidyl transferase which will insert multiple nucleotides at the 3' end of the labeled polynucleotide in the absence of a template strand). Other indirect tags include enzymes attached to a labeled polynucleotide (especially at a free end remote from the region paired to the probe) whose presence can be determined after displacement and separation steps of the embodied method by addition of the substrate for the enzyme and quantification of either the enzymatic substrate or, preferably, the enzymatic product. Similarly, the tag may be an apoenzyme, co-enzyme, enzymatic modifier or the like, with the other necessary reagents usually added with the appropriate enzymatic substrate, after displacement (and, in certain embodiments, separation). Of course, if the enzymatic reaction cannot occur with all but one component present (e.g., the substrate), then these other reagents may be present in solution during the displacement step (b) described above. Multiple tags can be added in manufacturing the labeled polynucleotide such as with a terminal deoxynucleotidyl transferase enzyme. Multiple labeled polynucleotides, e.g., one containing the enzyme (or apoenzyme) and one containing the coenzyme, may also be used. One form of attachment of the enzyme to the labeled polynucleotide is via affinity reagents, e.g., strepavidin/biotin. Such form could be used in embodiments wherein, for example, the complex is prepared by hybridizing a biotin-labeled polynucleotide to the probe and then binding strepavidin-enzyme to the biotin prior to the displacement step (b). Furthermore, as illustrated in FIGS. 3A-3D and discussed below, a moiety interacting with the tag in the complex may be present on the probe.

Most forms of tags, especially if remote from the pairing region of the labeled polynucleotide to the probe, will have little effect on the strength of base pairing between the labeled polynucleotide and the probe polynucleotide, as evidenced (for testing purposes) by little or no diminution of the reagent complex melting temperature and, more importantly, by negligible effects on the hybridization reaction between the target nucleotide sequence and the probe polynucleotide. Some forms of labeling, such as covalently bound biotin on nucleotides of the labeled polynucleotide in the pairing region and such as a large enzyme molecule or fluorescent moiety linked to nucleotides in or near the pairing region, may have an appreciable effect on reagent complex stability. Such effect generally will be to destabilize the labeled polynucleotide/probe polynucleotide binding (and thus lower is melting temperature). That effect may be somewhat beneficial in speeding up displacement, but can cause increases in non-specific dissociation or fall-off of the labeled polynucleotide. Such non-specific fall-off can usually be reduced, however, either by lowering the temperature during the displacement step, increasing the length of the labeled polynucleotide binding region, or other such physical means.

Forming the complex between an immobilized probe polynucleotide and labeled polynucleotide (such complex being provided in the present process and being in the present reagent) may involve attachment of the probe to a support (as described above) either before or after hybridization of the labeled polynucleotide to the probe polynucleotide. Affinity or other chemical reagents may be used for mediating or participating in such attachment. If the immobilization is completed after hybridization of the labeled polynucleotide to the probe polynucleotide, then the linking moiety or a part thereof can be already attached to the probe. Generally, the formation of such an immobilized complex will be followed by washing off unbound labeled nucleotide, and the conditions of such washing may be designed to also remove labeled polynucleotides that are only slightly bound (e.g. through less than about fifteen complementary bases elsewhere on the probe, instead of through the larger number of complementary bases at the desired binding site) or are adsorbed to the support. Probe polynucleotides and complexes of probe polynucleotide with labeled polynucleotide that are only marginally attached to the support may also be removed during this washing step. The washing should preferably be under sufficient conditions and for a sufficient time to substantially eliminate the non-specific background signal due to labeled polynucleotides (with or without probe polynucleotide) separating from the support independently of specific displacement during the displacement step of the present method. One can also use a reagent (e.g., protein) to block the non-specific binding sites on the support.

In the manufacture of complexes which are in solution when used, it is frequently also desirable to separate labeled polynucleotides which have not bound to probe polynucleotides from complexes (in some instances unbound probe polynucleotides may also be removed). Such separation may be by size alone (e.g., by size exclusion chromatography) if, as is frequently the case, the labeled polynucleotide is much smaller than either probe polynucleotides or complexes. Such separation may also be based upon the double stranded portion of the complex (at the labeled polynucleotide binding region of the probe) which is not likely to be present in either the labeled polynucleotide or probe polynucleotide which, except for small internal binding regions, will be in single-stranded form. This property renders complexes separable from unbound labeled polynucleotides by e.g., affinity chromatography using double-strand specific anti-nucleic acid antibodies or hydroxylapatite chromatography.

In some instances, the labeled polynucleotide and probe polynucleotide can be part of the same polynucleotide chain. For example, a linear single-stranded DNA molecule can be constructed from an M13 bacteriophage which contains a cloned DNA insert with terminal inverted repeats. These terminal inverted repeats, which are capable of forming a double-stranded region due to their complementarity, would include the labeled polynucleotide and the labeled polynucleotide binding region. Sequences located between these repeats would include the initial binding region, located adjacent to the labeled polynucleotide binding region. A unique restriction enzyme cleavage site, located within the outer edge of the terminal inverted repeats, could be cleaved to release the cloned insert from the single-stranded M13 vector backbone (c.f., G. A. Ricca, J. M. Taylor, & J. E. Kalinyak, Proc. Nat. Acad. Sci. (U.S.A.), vol. 79, pp. 724–728 (1982). An additional small inverted repeat sequence, containing a restriction enzyme cleavage site (e.g., the M13mp7 polylinker) could be placed at the inner edge of the labeled polynucleotide terminal repeat. Cleavage at such a site (e.g., X of FIG. 3D) will leave only complementary purine/pyrimidine base pairing to hold the labeled polynucleotide attached to the now distinct probe polynucleotide and will provide free ends on the probe polynucleotide through which attachment to a solid support may be mediated if so desired. Any tag or tags may be added to the labeled polynucleotide at this point if not already present.

The actual contacting or displacement step with sample material (potentially containing nucleic acids including the target nucleotide sequence) will normally be under conditions of temperature, ionic strength and time less stringent (and thus less conducive to uncoupling of the labeled polynucleotide) than the above washing step. A desirable temperature range during the contacting step is from about 15° C. to about 90° C., depending upon the solution ionic strength and other additives affecting melting temperature; the most efficient temperature will be one at which a maximum or near maximum rate of hybridization of sample nucleic acids to probe occurs. In certain cases, however, a more convenient (generally lower) temperature such as near ambient temperature (15°–25° C.) may be used. As described in a number of literature references (e.g., J. G. Wetmur and N. Davidson, *J. Mol. Biol.*, Vol. 31, pp. 349–370 (1968) and C. Minson and G. Darby, *New Developments In Practical Virology*, Vol. 1, p. 185–229 (1982, Alan Liss, Inc.), hybridization rate is also a function of pH and sample nucleotide concentration. Furthermore, it is preferred in at least some cases that a poly(alkylene oxide) which is a volume excluding polymer be present during this step. Other reagents such as dextran sulfate can be used as well. Enzymes and other proteins which affect the displacement process such as the *E. coli* ATP-dependent rec A protein (see Example 16) may also be present.

Proportions, amounts and concentrations of reagent complex are not independently critical, but it is generally desired that the total hybridization mixture of sample and reagent complex be as concentrated as feasible. In most instances, probe polynucleotides bearing binding sites for the target nucleotide sequence will also be present in ten-fold or more molar excess (preferably hundred-fold or more) of any expected level of target nucleotide sequence in the sample. The sample itself may include nucleic acids which preferably should be completely or partly in solution (separated from membranes and the like) and in single-stranded form for the hybridization step of the assay. The presence of the complement of the target nucleotide sequence (by virtue of denaturation of double-stranded sample DNA) could represent an interference. This interference is likely to be minor in at least the preferred forms of the invention; in hybridizations involving immobilization of the probe selectively (before or after displacement), displaced labeled polynucleotide will be and will remain in the solution phase and be subsequently determined, whether or not such displaced labeled polynucleotide has rehybridized with complementary segments of the sample nucleic acid. In many solution hybridizations this interference may be minimized by kinetic effects.

In general, displacement reactions should require no more than two hours, generally under one hour and frequently less than fifteen minutes to occur to a sufficient extent. Conditions can be adjusted to achieve substantial completion within these times. Longer incubation times are not disadvantageous, however. It is believed that the rate-limiting step is a sample or target nucleotide sequence finding a complementary sequence of the probe polynucleotide (cf. C. Green and C. Tibbetts, *Nucleic Acids Research, vol.* 9, pp. 1905–18 (1981)); once target/probe hybridization begins to occur, displacement of labeled polynucleotide is expected to occur in under one minute and frequently less than one second.

In some of the forms of the invention in which the complex is initially on a solid support, the liquid phase containing displaced labeled polynucleotide may be separated therefrom as a part of the determination step. If the complex is in solution, some forms of the invention involve treatments after the displacement step to fix complexes still present (and other forms of probe including those hybridized to a target nucleotide sequence) to a solid support, followed by a similar solid/liquid separation. Such separation of the solid phase containing bound complex from liquid phase containing displaced labeled polynucleotide may be by physical means such as chromatography, filtration, centrifugation or decantation. The solid phase may include magnetic or other separable particles that are attracted or otherwise physically removed from the liquid phase. Furthermore, complete separation of the two phases is not required; an aliquot of the liquid phase may be removed for determination, leaving the solid phase admixed with the remainder of the liquid phase.

If such a separation occurs, determination of the presence and (frequently) the quantity of labeled polynucleotide present may be conducted upon either phase, but is preferably conducted upon the liquid phase. Determination of the liquid phase for the presence and quantity of displaced labeled polynucleotide has the advantage of relatively low background signals. Any background signal will be largely that caused by non-specific fall-off from a solid support as described above or by imperfect separation. Additionally, the result of no target sequence in the sample is no signal from labeled polynucleotide in the liquid phase. By contrast, if detection were of the solid phase, maximum levels of labeled polynucleotide would be detected for a negative result. Especially when a high molar excess of reagent complex is used, measurements of a label remaining on the solid support results in reduced sensitivity.

If no separation is made, determination can still be made of displaced labeled polynucleotides. Some such determination steps involve a change in the signal detectable from a tag by virtue of displacement, including those signals affected by proximity of the tag to a signal-affecting moiety elsewhere on the labeled polynucleotide or on the probe polynucleotide (see description of FIGS. 3A-3D below).

In other forms, especially with immobilized probes, the interaction can be between two types of tag moieties. One type of tag can be on labeled polynucleotides hybridized to immobilized probe polynucleotides at one location on a solid support. A second type of tag may be on labeled polynucleotides which are hybridized to immobilized probe polynucleotides at a remote location on the same solid support. The second type of tag may also be otherwise directly attached to some remote location of the probe or of the same labeled polynucleotide or of the solid support. In all such cases involving two types of tags, the two different tags can interact only if at least one labeled polynucleotide is displaced. Such interaction is especially applicable to apoenzyme with coenzyme: e.g., apoglucose oxidase with flavin adenine dinucleotide (FAD).

The process and reagent of the present invention can be used for the detection and determination of a variety of target nucleotide sequences in a variety of concentrations. In particular, microorganisms including infectious agents whose nucleic acid (genomic or otherwise) could be targeted include pathogenic viruses, bacteria and fungi, e.g., cytomegalovirus or *Neisseria gonorrhea*. Exemplary genetic disorders or conditions which could be targeted include β-thalassemias, α₁-thalassemias, cri du chat syndrome and some retinoblastomas. The present process and reagents are applicable to detecting genetic disorders or variations primarily when a multi-base nucleotide deletion, insertion, substitution or transposition is involved in distinguishing the target nucleotide sequence from the closest sequence present in samples intended to be read as negative for the target sequence. To the extent that the present invention is applicable to genetic disorders due to single base mutations, if at all, the complement of the substituted base or other point of mutation is desirably part of the target binding region of the probe polynucleotide, with the location of that base within the region likely to affect the selectivity of the method. Among changes in structural or regulatory genes, changes or differences in the expression, activation or rearrangement of oncogenes can be detected by the present process, especially by targeting mRNA. Other perturbations in the expression of structural genes can be similarly detected. The present process can also be applied to HLA typing for tissue transplantation, determination of antibody resistance genes in microorganisms, and to the screening of food, medicinal and water samples for specific infectious agents or other microorganisms.

Selecting a target sequence for a particular test may involve determining a sequence which is unique or relatively unique to the target organism or condition. Such target sequence would be used to develop the target binding region as complementary thereto and then a labeled polynucleotide of appropriate length would be developed to bind to a part of the target binding region. In some instances multiple reagent complexes targeting different parts of the nucleic acid of the same organism or condition may be used in order to impart improved specificity when any particular target sequence is only relatively unique.

One embodiment of the present invention is illustrated, for purposes of understanding, by reference to attached FIGS. 1A-1E, in which is shown an immobilized probe polynucleotide P, 3300 nucleotides in length. Numbering from the 5' end, the region from nucleotide 3000 to nucleotide 3300 represents the target nucleotide binding region (TBR). For simplicity, it is assumed that the first nucleotide of the probe is directly attached to a support S. As illustrated in FIG. 1A, the labeled polynucleotide L consists of 150 bases to which a tag T is atttached at the 5' end. Of these 150 bases, 51 (from base number 100 to base number 150) bind specifically to the labeled polynucleotide binding region (LBR), bases 3250 to 3300, of the probe. Accordingly, when the immobilized probe consisting of probe polynucleotide P attached to support S is incubated with a solution of labeled polynucleotide L under normal hybridization conditions, a complex will be formed as shown in FIG. 1A with labeled polynucleotide L attached at the end of the probe polynucleotide P via base pairing between bases 3250-3300 of the probe P and bases 100-150 of the labeled polynucleotide L.

Figure 1B:
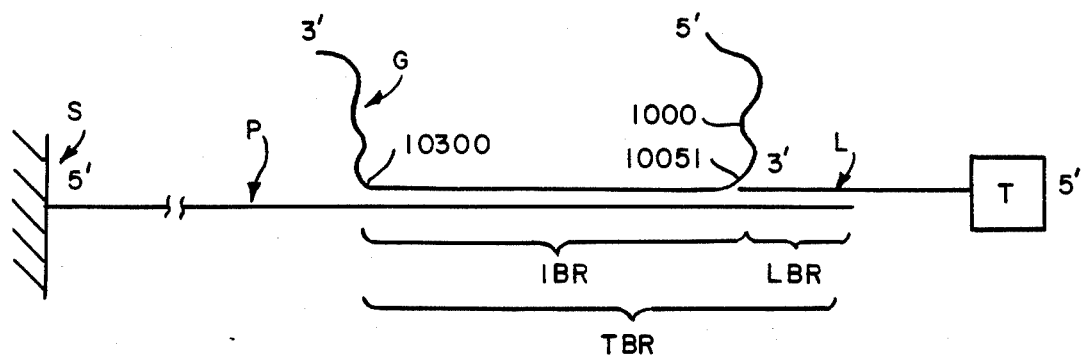
FIG. 1B is a view similar to FIG. 1A in which the reagent complex is hybridized with a target nucleotide sequence G of sample nucleic acid.

In use, the illustrative complex is contacted with a biological sample under hybridization conditions where the sample contains a nucleotide sequence with bases 10000 to 10300 of this sequence which corresponds to and binds selectively to the target binding region TBR of the probe. Under proper hybridization conditions, the sample polynucleotide G would first bind, as illustrated in FIG. 1B, between bases 10051 to 10300 of G and bases 3000 to 3249 (the initial binding region or IBR) of probe P (which IBR in the complex shown in FIG. 1A had been single stranded). It should be appreciated that thermodynamic considerations favor double-stranded moieties over single-stranded moieties. Thereafter, an equilibrium is created at bases 3250 to 3300 (LBR) of the probe polynucleotide P between binding to the labeled polynucleotide L and binding to bases 10000 to 10050 of the sample polynucleotide G. Under the conditions discussed below, a rapid zippering and unzippering will occur, as represented by the differences between FIG. 1B on the one hand and FIGS. 1C on the other hand. FIG. 1D shows the stage of near total displacement in somewhat enlarged and more graphic form. In such event, when additional bases of the sample polynucleotide G bind to the probe polynucleotide beyond probe base 3249, corresponding bases of the labeled polynucleotide L are displaced, creating a free end. Under the conditions described herein, this zippering and unzippering can occur in either direction; but the flavored event will be eventual shifting of the point of attachment to the right in FIG. 1C and down in FIG. 1D from base number 3275 on the probe P toward base number 3300, at which point the labeled polynucleotide L is totally displaced from the probe P (cf. FIG. 1E). It should be appreciated that, merely upon random zippering and unzippering in both directions, removal of the labelled polynucleotide L will be favored in that FIG. 1B represents the furthest to the left that the labeled polynucleotide L can displace the target nucleotide sequence of sample polynucleotide G. As long as some substantial region of initial binding region, IBR, exists in which a sequence of nucleotides of the probe polynucleotide P binds selectively to the target nucleotide sequence, but not to the labeled polynucleotide, displacement of the sample polynucleotide G completely from the probe will be a rare and reversible event.

An important parameter in optimizing the present method and reagent is the length and nature of the base pairing between the labeled polynucleotide and the probe polynucleotide. As compared to the 51 bases of exact pairing illustrated in FIG. 1A, modification may be made either by shortening or increasing this length, by introducing mismatches or loops in either strand or by selecting between DNA and RNA for either or both strands so as to affect the rate of spontaneous dissociation. In this regard, certain differences can be achieved when the target nucleotide sequence is RNA and the labeled polynucleotide is DNA, whether the probe polynucleotide P is either DNA or RNA. This is because, in general, RNA-RNA binding is strongest per base pair, DNA-RNA base pairing is of intermediate strength and DNA-DNA base pairing is of the least strength per base pair. If, however, the target binding region (TBR) is larger than the labeled polynucleotide binding region (LBR), then the labeled polynucleotide can be RNA and still be displaced by a DNA target nucleotide sequence. Targeting RNA may be required if, for example, the target microorganism is an RNA virus or the target condition is one of altered gene expression.

One means of reducing the binding strength in the region in which the labeled polynucleotide is bound to the probe polynucleotide is the introduction of individual base mismatches into the labeled polynucleotide. Assuming that the probe nucleotide sequence will be chosen to pair exactly or nearly exactly to the target nucleotide sequence, such mismatches can be considered as mutations or individual base substitutions in the labeled polynucleotide compared to a similar polynucleotide segment of the target nucleotide sequence which has exact or nearly exact binding. Such mutation or substitution may include the substitution of a natural or chemically modified nucleotide for a given natural nucleotide such as the following: G for A (to produce the opposite pair dG-rU, dG-dT, rG-dT or rG-rU), A for G, 5-methylcytosine for C, 5-hydroxymethylcytosine for C, gentibiosyl-5-hydroxymethylcytosine for C, or 5-bromouracil for A. In many preferred embodiments, such mutations involve the substitution of one naturally occurring nucleotide for another nucleotide. In certain such embodiments, the substitution involves the substitution of a pyrimidine for a purine, leading to a mismatched pair that has become a pyrimidine-pyrimidine pair. Because pyrimidines occupy less space than purines, such individual pyrimidine-pyrimidine mismatches can have a minimal effect upon adjacent nucleotide pairings. Purine-pyrimidine mispairings (for example, A being positioned opposite to C, or T or U being positioned opposite to G) are somewhat more space filling, but are still generally less space filling than the positioning of two purines (A-A, A-G or G-G) apposite each other. Counteracting the space-filling effect, however, is a stacking energy effect which runs in the opposite direction: generally, purine/purine base pairs display a lower free energy of stacking, purine/pyrimidine base pairs somewhat more and pyrimidine/pyrimidine base pairs somewhat more still. See R. L. Ornstein & J. R. Fresco, *Biopolymers*, Vol. 22, pp. 1979–2016 (1983) (two articles). The net effect, in terms of effect on melting temperature of the reagent complex, in terms of effect on stability of the reagent complex and in terms of effect on the displacement kinetics, will primarily represent a combination of these two counteracting effects, such that experimentation may be required to determine which, if any, mismatches may be preferably incorporated into the labeled polynucleotide for a particular probe after the position of the target nucleotide region and labeled polynucleotide region are fixed. An exemplary probe polynucleotide/labeled polynucleotide region containing a pyrimidine/pyrimidine mismatch at base 3275 (cf. FIG. 1A) is illustrated below:

| Probe - base: | 3270 | 3271 | 3272 | 3273 | 3274 | 3275 | 3276 | 3277 - |
|---|---|---|---|---|---|---|---|---|
| | G | C | A | T | G | C | G | T |
| | C | G | T | A | C | C | C | A |
| Labeled - base: | 130 | 129 | 128 | 127 | 126 | 125 | 124 | 123 - |

Examples 1-3 (among others) illustrate the use of a complex having a pyrimidine/pyrimidine mismatch. The entire labeled polynucleotide binding region for these Examples is indicated in Table I, and the corresponding sequences of the singly-mismatch labeled polynucleotide (L2 in Table 1) and of the perfectly matched labeled polynucleotide (L1 in Table 1) are also indicated. Example 9 illustrates (with sequences) two other labeled polynucleotides, one a perfectly matched 32-mer, the other having T substituted for C at two locations so as to form G-T mismatches.

In addition to point substitutions, mismatches can be created either by inserting a short sequence in the labeled polynucleotide L which does not correspond to the probe nucleotide sequence (e.g., inserting a series of A's between bases 125 and 126 of labeled polynucleotide L in the example illustrated in FIG. 1A) or by deleting a portion (such as by deleting bases 120–130 of labeled polynucleotide L in FIG. 1A). Insertions in the labeled polynucleotide will generally form a single-stranded loop or cruciform structure of the labeled polynucleotide; deletions therein will generally form a single-stranded loop or cruciform structure of the probe polynucleotide.

Such substitutions, deletions or insertions will have the effect of destabilizing the binding between the labeled polynucleotide L and the probe polynucleotide P such that the displacement of the labeled polynucleotide may be favored. It is important, however, to avoid to the extent possible nonspecific displacement of the labeled polynucleotide L from the probe polynucleotide P in the absence of the target nucleotide sequence. The minimum length of binding between the labeled polynucleotide L and the probe polynucleotide P which is sufficient to minimize such dissociation or falling off will be dependent on a number of factors including, especially, the conditions such as pH and temperature of hybridization, the mode of attachment of the probe polynucleotide to the support (e.g., end attachment versus nonspecific adsorption), the extent of destabilizing substitutions (or deletions or additions), the duplex base sequence at the region of hydrogen bonding and whether the binding is between RNA and RNA, DNA and RNA or DNA and DNA. The optimal conditions in a particular instance can be determined empirically with routine experimentation based upon the general teachings of the present disclosure. Such experimentation may involve melting temperature experiments with samples lacking the target nucleotide sequence for purposes of estimating stabilities, and then displacement experiments for final optimization.

In considering the geometric relationship between the region where the labeled polynucleotide binds to the probe polynucleotide (LBR) and the region where the target nucleotide sequence binds to the probe polynucleotide (TBR) a configuration such as that illustrated in FIGS. 1A–1B may be used, with the labeled polynucleotide binding region being a subset of and at the end of the target binding region distal to the solid support. A common end of the TBR and the LBR (probe nucleotide 3300 in FIG. 1A) may also be (or be near to) one end of the probe polynucleotide. There are, however, no great disadvantages in having the probe polynucleotide extend beyond this point in a sequence of a nonspecific nature. There may be situations in which it is desirable to have a probe polynucleotide continue beyond this pairing region and extend to a point of attachment of a tag (different from the tag T on labeled polynucleotide L) which is to be released subsequently by other techniques. Furthermore, the two tags (one on the labeled polynucleotide, the other in the probe polynucleotide) may interact, with the interaction being detected as a part of the read out. It may be preferred in certain embodiments of the invention that the labeled binding region be near or at the end of the target binding region nearest the support.

Situations which are included in the present invention, but which may be less preferred include extension of probe polynucleotide P beyond the LBR (that is, for example, for the 125 bases beyond base 3300 in FIG. 1F) with a region (such as bases 3375–3425) which binds selectively to a portion of the sample nucleotide (and especially a region such as bases 9750–9800 of the sample polynucleotide G). In such an event, the sample polynucleotide G could bind both at bases 3000–3249 of the probe polynucleotide P and at bases 3450–3500 of the probe polynucleotide P and overlay the labeled polynucleotide L. Such a structure, represented generally as a "triple-stranded" region or D loop (see C. Green and C. Tibbetts, *Nucleic Acids Research*, vol. 9, no. 8, pp. 1905–18 (1981), especially page 1912), might not cause displacement of the labeled polynucleotide L in certain topologies and thus would represent a potential specific binding event without a signal generation. While displacement at bases 3250–3300 of the probe might still be possible (and might even proceed from both ends), the loss of free movement of the sample strand G due to binding at its bases 9750–9800 may reduce the probability of complete displacement, especially when one considers at helical structures actually involved.

Figure 1C:
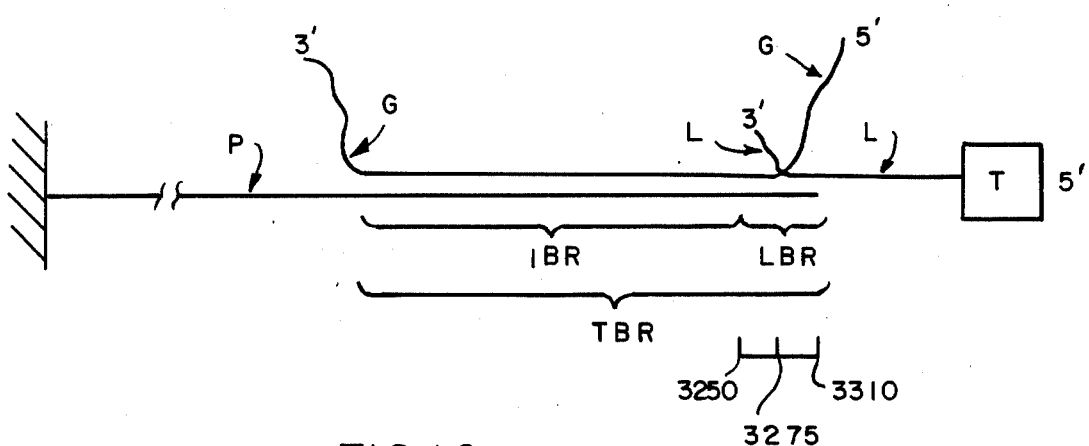
FIG. 1C is a view similar to FIG. 1B in which the sample nucleic acid has begun to displace labeled polynucleotide from the reagent complex.
Figure 1E:
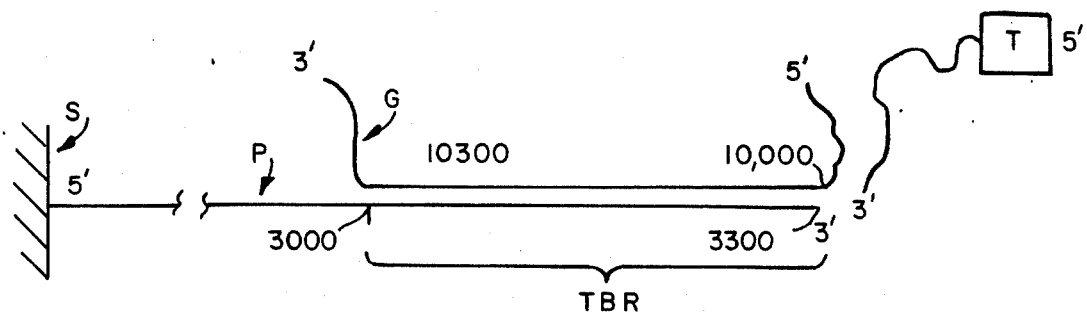
FIG. 1E is a view similar to FIG. 1C in which the labeled polynucleotide has been fully displaced from the reagent complex.
Figure 1F:
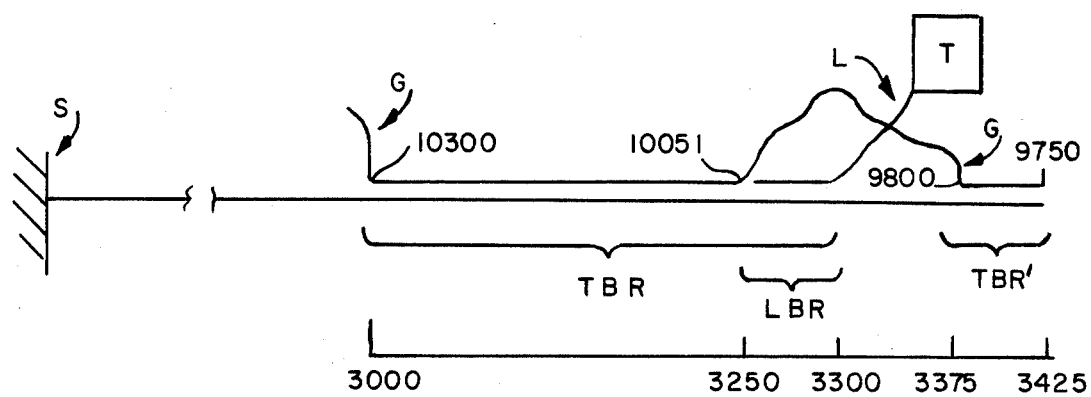
FIG. 1F is a view similar to FIG. 1B of a second embodiment of the present invention in which the immobilized polynucleotide has sequences complementary to and base paired with the sample nucleic acid on both sides of the region where the labeled polynucleotide is bound.
Figure 1G:
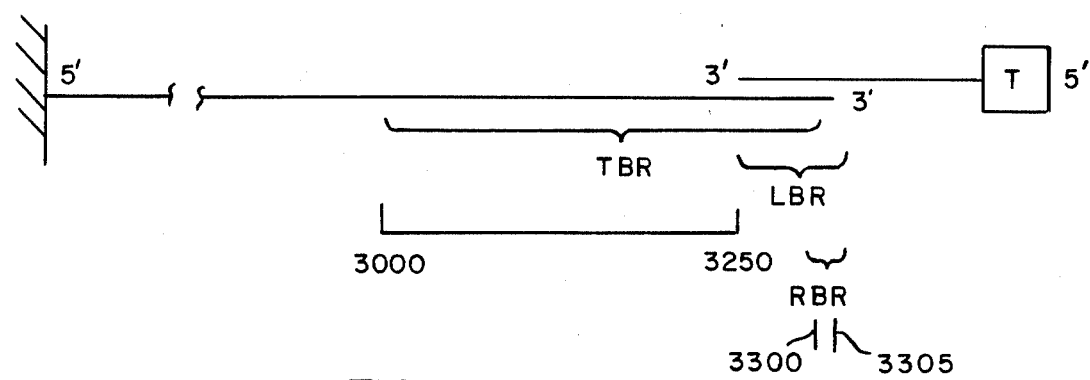
FIG. 1G is a view similar to FIG. 1A of a reagent complex according to a modification of the first embodiment.

Another situation within the scope of the present invention, but also somewhat less preferred than the above, is that in which the labeled polynucleotide binding region (LBR) extends beyond and outside the target binding region (TBR). This second embodiment of the invention is illustrated in FIG. 1G (and in Examples 13 and 14), wherein the reagent complex is shown, with the target nucleotide sequence being capable of displacing the labeled polynucleotide as far as the end of the TBR. The labeled polynucleotide would then remain bound via those probe bases which are part of the labeled polynucleotide binding region LBR but not part of the target binding region TBR (such sequence of bases being designated the residual binding region or RBR). Provided that the RBR (e.g., bases 3300 to 3305 of probe P in FIG. 1G) is much smaller than the LBR, one could, in theory, change conditions at this point (pH or temperature for example) so as to totally release the labeled polynucleotide L in this complex without releasing other labeled polynucleotides bound to the entire labeled polynucleotide sequence LBR (see Example 13 where this is described for a displacement in solution). One should consider, however, that the hybrid shown in FIG. 1G will still be capable of displacement to the left after complete binding of a target nucleotide sequence G, with the labeled polynucleotide capable of displacing part or all of the portion of the target polynucleotide sequence bound to bases within the overlap of TBR and LBR; such an event could be expected to lower the efficiency of displacing the labeled polynucleotide.

Other embodiments of the invention different from those illustrated in FIGS. 1A through 1G are illustrated in FIGS. 2–6 and discussed briefly below.

Figure 2:
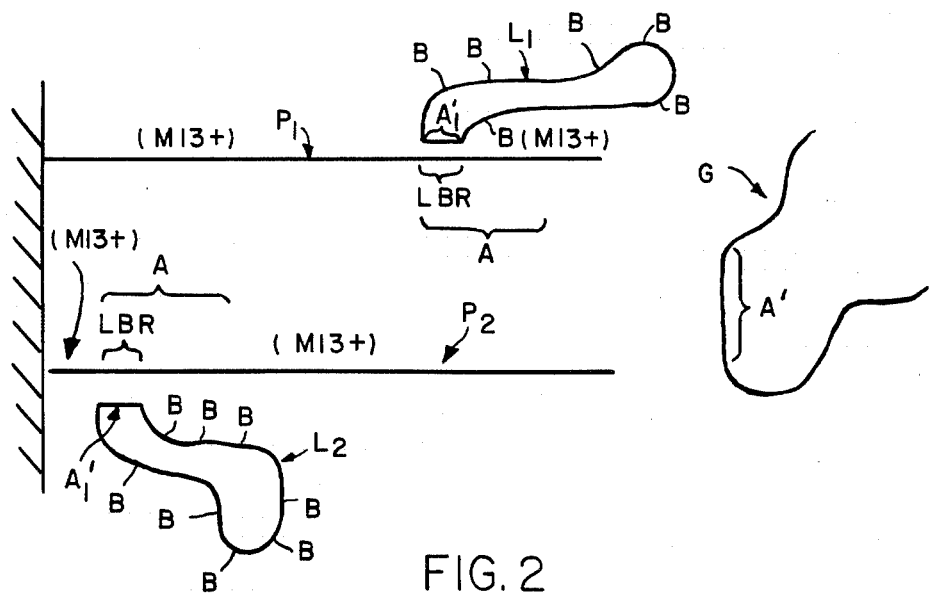
FIG. 2 is a view similar to FIG. 1A of a reagent complex according to a third embodiment of the present invention, with a sample polynucleotide having the target nucleotide sequence shown prior to hybridization to the reagent complex.

FIG. 2 illustrates a third embodiment of the invention using a complex different from that of FIG. 1A in that the labeled polynucleotide $L_1$ is the circular plus (or infectious) strand (M13+) of DNA bacteriophage M13 into which is inserted a segment $A_1'$ complementary to a portion (LBR) of the target binding region A of the probe strands $P_1$ and $P_2$. The label in this embodiment is shown as a series of biotin moieties B distributed within the M13+ major portion of the labeled polynucleotide $L_1$, possibly by growing M13 in bacterial culture with biotinated nucleotide triphosphate (e.g. biotinated-dATP) present or by chemically attaching biotin afterwards to the M13 nucleotides. The $A'_1$ segment may also contain nucleotides bound to biotin. The sample polynucleotide G will, in this instance (FIG. 2), contain a target nucleotide sequence A' complementary to segment A of each probe $P_1$ and $P_2$. In this embodiment the probe polynucleotides may also be formed using bacteriophage M13, with segment A complementary to the target nucleotide sequence A' inserted at a location in the non-essential region of the M13 genome. The M13+ segments of the probe are non-complementary (actually equal or homologous) to M13+ regions of the labeled polynucleotide. If the circular phage is cleaved non-specifically (e.g., by partial cleavage with restriction enzyme Hae III; c.f. R. W. Blakesley and R. D. Wells, *Nature*, vol. 257, pp. 421–422 (1975)), linear strands will be created having segment A positioned at different points relative to the ends, but generally with a portion of the M13+ strand on both sides of segment A. This is illustrated in FIG. 2 by strand $P_1$, wherein the segment A is close to the free end of supported polynucleotide, and strand $P_2$, wherein segment A is close to the attached end. Of course, cleavage will also potentially produce shortened strands (due to two or more cleavages in the M13+ region) and could also produce strands with region A split between the two ends (due to cleavage in region A); the latter condition can result in failure to form a complete and fully operative target binding region. So long as region A is small relative to the length of the M13+ strand (7.2 kilobases; J. Viera & J. Messing, *Gene*, vol. 19, 259-68 (1982)), relatively few probe strands would be expected to have region A split. Uniformity in location of segment A can be achieved by cleaving single-strand M13 DNA specifically (e.g., with a restriction enzyme recognizing an inverted repeat sequence in or inserted into the M13 genome).

After displacement, the biotinated displaced labeled polynucleotides of FIG. 2 or related embodiments could be concentrated from the liquid phase, e.g., with a strepavidin column, before readout using, e.g., horseradish peroxidase linked to strepavidin and colorimetric, fluorimetric or chemiluminescent readouts based upon the peroxidase activity.

Figure 3A:
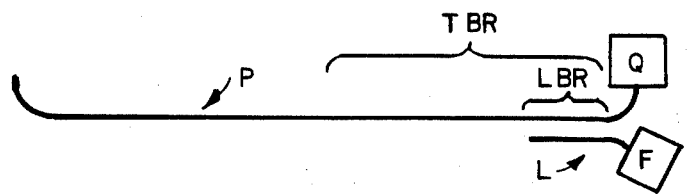
FIG. 3A is a view similar to FIG. 1A of a reagent complex according to a fourth embodiment of the present invention.

FIG. 3A illustrates a fourth embodiment of the present invention with the reagent complex entirely in solution (no support is present). The probe polynucleotide P has a target binding region (TBR) including a subregion, the labeled polynucleotide binding region (LBR), in which bases are bound to complementary bases of the labeled polynucleotide (L). The labeled polynucleotide (L) contains a fluorescent tag (F) held in the complex in close proximity to a quencher moiety (Q) attached to the probe (P). These moieties F and Q are sufficiently close in the complex of FIG. 3A for any signal produced by stimulation of the fluorescent tage (F) by radiation to be absorbed by the quencher moiety (Q). An exemplary pair of F and Q are fluoroscein with rhodamine. See M. Cobb and S. Gotcher, *Am. J. Med. Tech.*, Vol. 48, No. 8, pp. 671-677 (1982).

Figure 3B:
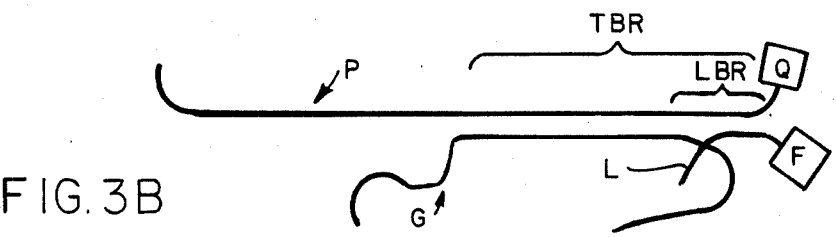
FIG. 3B is a view similar to FIG. 1C of the fourth embodiment of FIG. 3A.
Figure 3C:
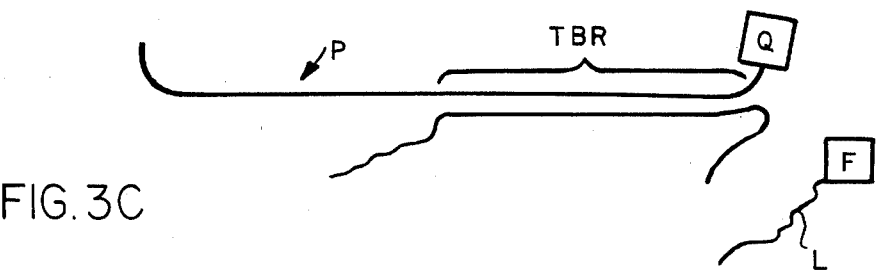
FIG. 3C is a view similar to FIG. 1E of the fourth embodiment of FIG. 3A.

FIG. 3B illustrates the reagent complex of FIG. 3A after contact by a sample G containing the base sequence complementary to the entire target binding sequence (TBR). As in FIG. 1B, binding will be first to the unpaired region of TBR and then displacing portions of the labeled polynucleotide L from the subregion LBR. The stage of partial displacement (such as seen in FIGS. 1C and 1D) is illustrated in FIG. 3B. Upon completion of the displacement, the target sequence of sample polynucleotide G will be bound to the entire region TBR of probe P and the labeled polynucleotide L will be totally displaced. In this situation, as illustrated in FIG. 3C, the tag (F) is now sufficiently far from quencher moiety (Q) to produce a detectable signal on stimulation that is not quenched (except in those rare cases where another probe P happens to be located such that its label Q is in close proximity to tag F). Accordingly, the stimulation of fluorescent tag (F) and measurement of unquenched signals can serve as a quantitative detection method for displaced labeled polynucleotides without a separation step having been performed.

Figure 3D:
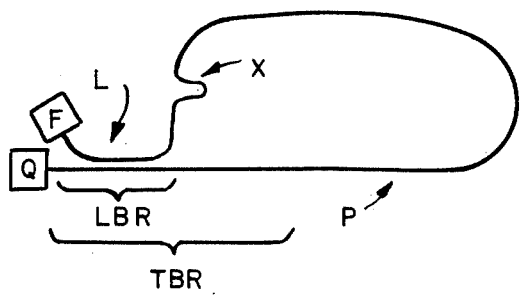
FIG. 3D is a view similar to FIG. 3A of a modified form of the reagent complex of the fourth embodiment.

A modification in the embodiment of FIGS. 3A—3C in which the labeled polynucleotide L and probe polynucleotide P (bearing, respectively, labels F and Q) are part of the same molecule is illustrated in FIG. 3D. In addition, a site X is shown which contains an inverted repeat sequence a portion of which is recognizable by a restriction enzyme. Cleavage by such an enzyme can be used to sever the covalent linkage between TBR and L (although this severing is not required when the readout is based upon the F-Q interaction). Such cleavage can also be used as a first step in creating a site for attachment of the probe to a support, such attachment to occur before or after displacement. The overall geometry of FIG. 3D may thus be used in synthesizing reagent complexes as a single molecule for various embodiments, including those of FIGS. 1A-1E.

Figure 4:
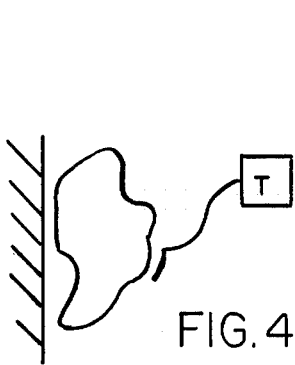
FIG. 4 is a view similar to FIG. 1A of a reagent complex according to a fifth embodiment of the present invention.

FIG. 4 illustrates a complex in which the probe strand $P_3$ is a circular single-stranded polynucleotide non-specifically adsorbed on support S. Such a polynucleotide can be produced by insertion of a target binding region (TBR), into a single-stranded bacteriophage such as M13 through suitable cloning procedures. The labeled polynucleotide L here contains a segment $A'_1$ complementary only to a portion LBR of segment TBR.

Figure 5:
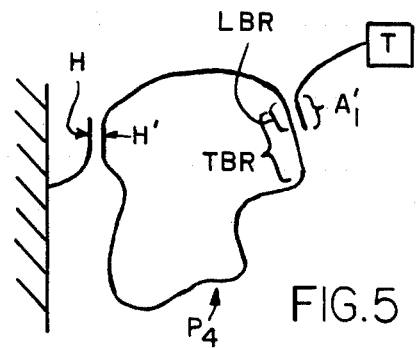
FIG. 5 is a view similar to FIG. 1A of a reagent complex according to a sixth embodiment of the present invention.

FIG. 5 illustrates a complex similar to FIG. 4 except that, instead of being adsorbed to support S, probe strand $P_4$ is linked via a linking polynucleotide covalently attached to support S. Such linking polynucleotide contains a region H complementary to a segment H' of the probe $P_4$ remote from the TBR segment.

FIG. 6 illustrates a complex similar to the embodiment of FIG. 1A in that the probe strand $P_5$ contains a target binding region TBR near or at its free end. A number of portions of the TBR segment (subsegments $A_3$, $A_4$, $A_5$, $A_6$, $A_7$, $A_8$, $A_9$, and $A_{10}$) are each base paired to a complementary region of a labeled polynucleotide: segment $A'_3$ of labeled polynucleotide $L_3$ to subsegment $A_3$, etc. Probe $P_5$ contains a target binding region TBR divided into subsegments $A_1$ and $A_2$, together forming the initial binding region, as well as eight additional subsegments ($A_3$ thru $A_{10}$), each forming a labeled polynucleotide binding region. In this embodiment, binding of segment A' of the sample polynucleotide G (as shown in FIG. 1E) will displace all of the labeled polynucleotides $L_3$, $L_4$, $L_5$, $L_6$, $L_7$, $L_8$, $L_9$ and $L_{10}$ and thus produce an enhanced signal compared to the situation shown in FIG. 1A. It should be appreciated, however, that the absence of any of those labeled polynucleotide (e.g., $L_8$) could permit the target nucleotide to form D-loops (as in FIG. 1F) by binding to subsegments $A_1$ and $A_2$ (for which no labeled polynucleotide is complimentary) and any other probe subsegment (e.g., $A_8$) for which the labeled polynucleotide is absent on that particular probe strand.

EXAMPLES

In certain of the following examples, four small synthetic DNA oligomers were used as the tagged polynucleotides; all were labeled with radioactive phosphorous-32 atoms. Two oligomers were 27 base oligomers matching 26 or 27 bases at the 3' end of one strand of a 1.1 kb pBR322 DNA fragment. This fragment stretched from the Pst I restriction site to the Bam HI restriction site in pBR322 DNA. These two oligomers (L1 and L2), and the labeled polynucleotide binding region to which they were bound, are illustrated in Table 1. The mismatched pyrimidine base in oligomer L2 is underlined.

TABLE 1

```
                        350
Probe  5' end ... T—A—C—G—C—G—A—T—G—A—
L1                         3' C—T—A—G—T—
L2                         3' C—T—A—G—T—
                                          360              367
Probe  T—G—C—G—A—C—C—A—C—A—C—C—C—
L1     A—C—C—G—C—T—G—G—T—G—T—G—G—G—
L2     A—C—C—G—C—T—G—G—T—G—T—G—G—C—
       20                               10   9
                        370
Probe  G—T—C—C—T—G—T—
L1     C—A—G—G—A—C—A—
L2     C—A—G—G—A—C—A—
                        380
Probe  —G—G—A—T—C—C ... 3' end
```

TABLE 1-continued

| | |
|---|---|
| L1 | —C 5' end |
| L2 | —C 5' end |

The two oligomers used in other examples were 32 base oligomers matching a region near the middle of a 1.1 kb human albumin gene sequence. The two oligomers (L3 and L4) were, respectively, perfectly matched or containing two mismatches (see Example 9 for the sequences of L3 and L4).

EXAMPLE 1

Detection of Oligomer Displacement in Solution by Sepharose 4B Gel Filtration

The 27 base oligomer containing a single mismatch (L2 in Table 1) was kinased using $^{32}$P-δ-ATP and hybridized to the + strand of M13mp9 clone II-16 DNA. M13mp9 clone II-16 DNA consists of bacteriophage M13mp9 DNA into which has been cloned the 1.1 kb Pst I-BamH1 fragment of pBR322 oriented such that the plus strand contains the Bam HI site at its 3' end. Bound oligomer was then purified on a Sepharose® 4B column to remove unbound oligomer from the reagent complex. Approximately 40% of the probe molecules were found to be hybridized with labeled oligomer. About 250 ng of the reagent complex were exposed to a 5-fold molar excess of single-stranded competitor M13mp8 clone 20 DNA or non-homologous M13mp8 DNA, at 41° C. in the presence of 2X SSC for 20 min or 2 h. The plus strand of M13mp8 clone 20 DNA consists of bacteriophage M13mp8 DNA into which has been cloned the 1.1 kb DNA strand complementary to the pBR322 DNA present in M13mp9 clone II-16. Portions of each sample were removed for gel electrophoresis and autoradiography (data not shown, but they confirmed the subsequent analysis). The remaining samples (5500–8000 cpm total activity were applied to a 5 ml Sepharose® 4B column. Three drop fractions were eluted in TE (10 mM Tris, pH 8.0, 1 mM Na$_2$EDTA) and counted with scintillant. The results are summarized in Table 2.

TABLE 2

| | Percent Total Counts | |
|---|---|---|
| Sample | Early peak (bound oligomer) | Late peak (free oligomer) |
| 1. original unchallenged reagent complex; 2h, 41° C. | 68% | 32% |
| 2. reagent complex + 5-fold molar excess of M13mp8 clone 20 DNA; 20 min., 41° C. | 27 | 73 |

TABLE 2-continued

| | Percent Total Counts | |
|---|---|---|
| Sample | Early peak (bound oligomer) | Late peak (free oligomer) |
| 3. reagent complex + 5-fold molar excess of M13mp8 clone 20 DNA; 2h, 41° C. | 5 | 95 |
| 4. reagent complex + 5-fold molar excess of non-homologous M13mp8 DNA; 2h, 41° C. | 71 | 29 |

EXAMPLE 2

Effect of Simple and Complex Non-homologous DNA Upon the Displacement of Release Tag by Competitive DNA, Release Tag at End of Target Binding Region Purified reagent comprised of single-stranded M13mp9 clone II-16 DNA (See Example 1) and kinased 27-mer containing a single mismatch (labeled polynucleotide L2 in Table I, above) were prepared as described in Example 1. Competitive hybridizations were carried out at 50° C. in the presence of 2X SSC for up to 1 h; samples were held on ice until subjected to electrophoresis on a 1.5 mm thick 5% (top) and 20% (bottom) stacked polyacrylamide gels. Electrophoresis was conducted for about 600 V-h and the stacked gel system was autoradiographed. Each sample contained 50 ng of the release tag-probe complex; M13mp8 clone 20 DNA served as the sample competitor DNA, while M13mp8 DNA and sheared calf thymus DNA were non-homologous additions. Table 3 summarizes the identity of samples loaded in individual polyacrylamide gel wells and the percent of free or unbound labeled oligomer. The percent oligomer values are derived from densitometric tracings of the autoradiogram taken for each gel lane.

TABLE 3

| Lane | Sample Nucleic Acid | Time of Competitive Hybridization | Percent Free Oligomers |
|---|---|---|---|
| 1. | orig. hybrid, unchallenged | — | 8 |
| 2. | 250 ng competitor DNA + 1500 ng M13mp8 | 10 min | 87 |
| 3. | 250 ng competitor DNA + 1500 ng M13mp8 | 1 h | 97 |
| 4. | 1500 ng M13mp8 DNA | 1 h | 3 |
| 5. | no competitor DNA | 1 h | 4 |
| 6. | 2000 ng calf thymus DNA | 1 h | 3 |
| 7. | 250 ng competitor DNA + 2000 ng calf thymus DNA | 10 min | 77 |
| 8. | 250 ng competitor DNA + 2000 ng calf thymus DNA | 1 h | 98 |
| 9. | 250 ng competitor DNA | 10 min | 69 |
| 10. | 250 ng competitor DNA | 1 h | 98 |

The percent free oligomer values show that a substantial excess of M13mp8 DNA or complex calf thymus DNA does not cause significant non-specific displacement of the oligomer (labeled polynucleotide) and does not inhibit the rapid displacement caused by competitor DNA (the target nucleotide sequence).

EXAMPLE 3

The Effect of Base Pair Mismatches on the Kinetics of Oligomer Strand Displacement The rate of displacement of a 27-base oligomer containing a single mismatch (L2, Table 1) was compared to that of a perfectly matched oligomer (L1, Table 1) bound to the same probe polynucleotide sequence. Oligomers were kinased using 32P-γ-ATP to specific activities of $1-2\times10^8$ cpm/μg. Single-stranded probe DNA was prepared by standard procedure from M13mp9 clone II-16 (see Example 1). About 5 μg of the probe polynucleotide were hybridized with 45 ng of either perfect or single-mismatch-containing oligomers (see Table 1) by heating the mixture in the presence of 0.5M NaCl to 65° C. and allowing the solution to cool slowly to room temperature. The hybridized oligomer (reagent complex) was separated from free oligomer by elution from a Sepharose 4B column; approximately 50% of the probe molecules were found to be hybridized to oligomer.

Competition hybridizations were performed at 60° C., in a final volume of 5 μL, containing 2X SSC and 25 ng of the reagent complex. 25 ng of single-stranded M13mp8 clone 20 DNA (see Example 1) served as the competitor DNA having the target nucleotide sequence; nonhomologous "competitor" DNA was from bacteriophage M13mp8 viral particles. Samples were placed on ice after incubation for desired periods, and subjected to electrophoresis in a 15% polyacrylamide gel. The area under peaks resulting from densitometric scans of an autoradiogram obtained from the gel were then quantitated. The fraction of total counts which appears as free oligomer (high mobility) and as reagent complex (low mobility) is tabulated below in Table 4 as a function of time of incubation.

TABLE 4

| | % Total cpm | | | |
|---|---|---|---|---|
| | Low Mobility | | High Mobility | |
| Incubation Time | Perfect | Mismatch | Perfect | Mismatch |
| 1. 1x competitor, 0 min | 100 | — | 0 | — |
| 2. 5 min | 87 | — | 12 | — |
| 3. 15 min | 74 | — | 25 | — |
| 4. 30 min | 60 | 42 | 39 | 58 |
| 5. 1 h | 38 | 37 | 62 | 63 |
| 6. 2 h | 42 | 23 | 57 | 77 |
| 7. 3 h | 42 | 0 | 58 | 100 |
| 8. No competitor, 3 h | 100 | 81 | 0 | 18 |

While 50% of the perferctly matched oligomer is displaced at approximately 40 minutes, about 30 minutes is required to displace specifically 50% of the single mismatch-containing oligomer at the constant reaction temperature of 60° C.

EXAMPLE 4

Effect of Non-Homologous DNA on Release Tag Strand Displacement in Solution, Release Tag Internal to Target Binding Region An M13 clone containing approximately 1100 bases of an albumin cDNA clone as an insert (representing the target binding region of 1.1 kb in length) was prepared for use as the probe polynucleotide strand. An oligonucleotide 32 bases in length (L3 of Example 9) and complementary to a 32-nucleotide sequence (the labeled polynucleotide binding region) near the middle of the 1.1 kb insert (target binding region) was end-labeled with phosphorous-32 (to be used as the labeled release tag polynucleotide) and hybridized to the M13 probe so as to form a reagent complex. Unhybridized 32-mer was removed by two passages through a 10 cm Sepharose ® CL-4B column equilibrated in 0.3M NaCl, 10 mM Tris and 0.1% SDS. The specific activity of the reagent complex was approximately 1000 cpm per ng of probe DNA. Approximately ⅓ of the probe strands had a labeled 32-mer polynucleotide bound. About 10 ng of the reagent complex was then combined in a 20 μl volume of 1M NaCl, 50 mM Tris with one of the following:

(A) 1000 ng sheared, boiled herring sperm (HS) DNA
(B) 100 ng boiled, linearized plasmid Alb5/RII DNA containing albumin coding sequence on a 1400 nucleotide fragment (this coding sequence has a portion complementary to the 1.1 kb cloned insert in the above M13 clone and thus represents the target nucleotide sequence);
(C) 100 ng of DNA from another M13 clone containing the opposite strand of albumin coding sequence than is present in the probe. This M13 DNA was digested with the restriction endonuclease HaeIII to linearize the DNA and to produce a linear fragment (2A/Hae III) containing a 1.72 kb albumin gene sequence which includes a contiguous sequence complementary to the 1.1 kb target binding region sequence).
(D) 100 ng of DNA (4A/Hae III) as in C above except that the sequence of DNA coding for albumin that is present is the same as the target binding region in the probe complex.
(E) No additional DNA, with incubation.
(F) No additional DNA; no incubation.

Each of the above solutions was incubated at 50° C. for two hours (except for F). Following incubation, each sample was electrophoresed on a 2.5% agarose gel and the gel was autoradiographed. Several autoradiographs of varying exposure length were prepared. The results with the longest exposure (66 hrs with 2 intensifying screens) indicate that in the absence of true competitor DNA or in the presence of non-homologous competitor, no displacement of the release tag oligonucleotide occurs. However, in the presence of specific competitor, all (in case C) or almost all (in case B) of the release tag oligomer can be displaced. An exposure suitable for densitometry (98 hrs with no screen) was quantified by scanning densitometry. The peaks were carefully cut out of the gel scan, weighed, and the percentage of mass in the intact hybrid (I) and the displaced strand (D) peaks were determined; the results are summarized in the middle columns of Table 5. Following autoradiography, the gel was aligned with the autoradiogram and the regions of the gel containing the radioactivity were excised and counted by liquid scintillation counting. All samples were counted for 20 minutes. The background counts were 25 cpm. This background was substracted from all samples resulting in the data in the righthand columns of Table 5. The quantification in Table 5 verifies the visual result seen and scored in the autoradiogram; that is, major amounts of displacement occurred only in those runs (cases B and C) in which the complex was contacted with DNA containing a target nucleotide sequence that could bind to the target binding region of the reagent complex.

TABLE 5

| Quantitated Strand Displacement in Solution | | | | | |
|---|---|---|---|---|---|
| | | | mass(ng) | % | cpm | % |
| A | HS DNA | I | 85.7 | 100 | 245 | 100 |
| | | D | 0 | 0 | 0 | 0 |
| B | Alb 5/RII | I | 25.6 | 32 | 60 | 41 |
| | | D | 54.2 | 68 | 87 | 59 |
| C | 2A/HaeIII | I | 7.1 | 10 | 19 | 24 |
| | | D | 66.0 | 90 | 61 | 76 |
| D | 4A/HaeIII | I | 73.5 | 100 | 250 | 100 |
| | | D | 0 | 0 | (−2) | 0 |
| E | NO DNA-2 hr | I | 70.1 | 100 | 218 | 100 |
| | | D | 0 | 0 | 0 | 0 |
| F | NO DNA-0 hr | I | 86.4 | 100 | 200 | 100 |

TABLE 5-continued

| Quantitated Strand Displacement in Solution | | | |
|---|---|---|---|
| mass(ng) | % | cpm | % |
| D  0 | 0 | 0 | 0 * |

EXAMPLE 5

Effect of Topology on Rate of Strand Displacement Circular or Linear Probes of Identical Sizes with Circular or Linear Displacing Strands The probe was a piece of human albumin cDNA (see Example 15) cloned into an M13mp9 vector. Adjacent to the albumin insert was the polylinker from M13mp7 which consists of an inverted repeat containing restriction endonuclease cleavage sites for several enzymes. In the single stranded, this inverted repeat forms a double-stranded region due to complementary base pairing. The circular strand can be linearized at that polylinker sequence by digesting with one of the appropriate enzymes (for example Bam HI). Circular M13-albumin DNA or such DNA linearized by digestion with restriction enzyme Bam HI was then annealed to a phosphorus-32 labeled 375 nucleotide fragment of human albumin DNA prepared as described in Example 4. Competitor DNA strands were either from M13mp8 clone containing the DNA insert strand of complementary sense to that of the albumin sequence in the reagent complex (circular competitor) or a linear 840 bp fragment of the albumin cDNA denatured by boiling and immediately quenching on ice (linear competitor).

Displacement reactions were set up in a standard hybridization buffer with either the circular or linearized reagent complex and one of the following:

[a] no DNA
[b] 10 ng circular competitor
[c] 100 ng circular competitor
[d] 1 ng linear competitor
[e] 10 ng linear competitor Reactions were carried out for 5, 15, 30, or 60 minutes. Following completion of the reactions, the samples were electrophoresed and autoradiographed as described in Example 4.

With the circular competitor, the topology had a dramatic effect: the circular competitor displaces the probe from the circular hybrid at a rate much slower than from the linear hybrid. With the linear competitor, the effect of probe topology is still observable, although not to a significant extent. There is only marginally better displacement from the linear hybrid than from the circular hybrid. Thus, when two circles are interacting, the rate of displacement is slower than when a linear and a circular molecule or two linear molecules are hybridizing during a displacement reaction.

EXAMPLE 6

Displacement From A Supported Complex

The reagent complex described in Example 4 (10 ng) was adsorbed on Schleicher and Schuell NA45 paper (DEAE cellulose/nitrocellulose paper), air dried, and then irradiated with ultraviolet light (handheld short wavelength UV lamp held at a distance of 0.5 cm) for 0, 1, or 5 minutes. The filters were then incubated in a small volume of hybridization solution at 50° C. for 4 hours. An aliquot of each solution phase was saved for electrophoresis, and the remaining solution removed and saved. Incubation of all filters was then continued overnight in fresh hybridization solution and aliquots were saved. Displacement reactions were carried out for 4 hours at 50° C. with 100 ng of various sample nucleotide strands. An aliquot of each reaction solution phase was again saved for gel electrophoresis and the remainder was counted by liquid scintillation counting for two minutes (no background counting was done). All appropriate samples were electrophoresed on the same 2.5% agarose gel and the gel was autoradiographed. The results indicate that some of the composite reagent complex and some 32-mer came off the filters in the first 4 hours preincubation. The UV treatment for 5 minutes substantially decreased the amount of complex which came off, although a small amount of 32-mer did still come off. During the subsequent overnight incubation, very few additional counts came off according to the results of liquid spectrometry (Table 6). During the displacement reactions, the 32-mer labeled polynucleotide was specifically displaced only when the correct competing DNA strand (containing the 1.1 kb target nucleotide sequence) was present (Table 6, sample competitor 2A/H); and essentially no displacement was detected with either no competitor DNA (No Comp) or a large excess (1000 ng) of non-specific herring sperm competitor DNA (HS DNA).

TABLE 6

| | Competitor DNA | # cpm in reaction solution phase |
|---|---|---|
| 0' UV | 2A/H | 1777 |
| | No Comp | 607 |
| | HS DNA | 714 |
| 1' UV | 2A/H | 2261 |
| | No Comp | 96 |
| | HS DNA | 154 |
| 5' UV | 2A/H | 2267 |
| | No Comp | 260 |
| | HS DNA | 272 |

EXAMPLE 7

A portion of pBR322 located between the Eco RI and Sal I restriction sites (about 650 bases in length) was cloned into M13mp8 or M13mp11 (see Example 13). Using a $^{32}$P-end labeled 27 nucleotide long oligonucleotide complementary to a portion of this pBR322 sequence as primer and the appropriate template chosen from the above two clones, DNA synthesis was initiated on the template and extended partially around the circle. The DNA was digested with Eco RI and the resulting 375 nucleotide end-labeled fragment was purified by denaturing agarose gel electrophoresis. This 375-mer was annealed back to the pBR322/M13 probe strand to form a reagent complex wherein the labeled polynucleotide was bound to the end 375 nucleotides of a 650 nucleotide target binding region. Unannealed 375-mer was removed by a Sepharose ® CL-4$_B$ column as described in Example 4. This reagent complex (10 ng) was then used in a strand displacement reaction at 70° C. in 0.4M NaCl, 100 mM Tris. The sample competitor DNA used in each of the five runs was:

(A) no DNA
(B) 10 ng of circular M13mp11 into which had been cloned pBR322 DNA complementary to the target binding region over most of its 650 base length; this DNA thus contains the 650 base long target nucleotide sequence in an 7800 base long circle.
(C) 100 ng of the same 7800-mer circular DNA as in B;

(D) 100 ng of circular M13 into which had been cloned a pBR322 DNA strand identical to that found in the probe strand (and thus does not contain the target nucleotide sequence); and (E) 15 ng of a linearized, denatured 650 base long Eco RI/Sal I fragment of pBR322 (containing the 650 base long target nucleotide sequence as a singlestranded linear DNA molecule as well as its 650 base long complement).

After 0', 5', 15', 30' and 60', the displacement reactions were stopped by quenching on ice; and at the end of the experiment, the samples were electrophoresed on a 1.5% agarose gel and autoradiographed. There was a slight contamination with unannealed 375-mer still present (i.e., a background value of radioactivity was seen at the location for 375 nucleotide length pieces in Case A). No increase in this background was observed over the 60' reaction, either with the negative controls of no competitor DNA (Case A) or with the same strand as sample competitor DNA (Case D). Specific displacement was observed with the opposite strand as competitor (Cases B and C) or with the denatured, linearized fragment (Case E). The ability to quantitate the results of this experiment are complicated by the existence of a doublet of uncertain origin in all cases in the low mobility gel region. Qualitatively, it appeared that the approximately equimolar competitor: reagent ratio of Case B yielded less complete and less rapid displacement compared to the 10:1 molar ratios of Cases C and E (note that the negative control Case D was also at a 10:1 molar ratio). Where displacement occurred in Cases B and C, two new locations of peak radioactivity occurred: one at a lower mobility (higher molecular weight) than the initial complex (presumably an intermediate structure such as in FIG. 3B, but with both probe P and competitor G being circular), the other at the higher mobility (lower molecular weight) of displaced 375-mer. The stability of the intermediate structure is presumably due to the circular nature of the probe strand and competitor (see Example 5). Case E does not show the appearance of significant amounts of the lower mobility peak because the challenger is linear in Case E, but does show a second high mobility peak. This second high mobility peak probably results from rehybridization of the displaced labeled 375-mer to the 650 base-long complementary DNA strand present because of the use of denatured double-stranded DNA as sample competitor DNA in Run E.

EXAMPLE 8

Reagent Complex Melting Temperatures and Temperature Effects on Fall Off Rate and Competitive Displacement Rate Hybrids between M13mp9 lone II-16 DNA (see Example 1) and the 27 base oligomer containing a single mismatch (L2, Table 1) were purified as described in Example 1. Samples of the hybrid (25 ng of reagent complex) were exposed to several desired temperatures for 10 min. in the presence of 2X SSC, and subjected to electrophoresis on a stacked 5% (top) and 20% (bottom) polyacrylamide gel. The resulting gel was autoradiographed at −80° C. with Kodak X-ray film and a Dupont Cronex intensifying screen. No increase in the proportion of label found in the small high mobility (unbound oligomer) band was seen until 65° C. was reached, and the Tm (temperature at which half the oligomer has been melted off) was calculated to be about 68°. In this autoradiogram, lane 1 represented original hybrid, lanes 2-9 represented competitive displacement reactions at 40° C., 45° C., 50° C., 54° C., 57° C., 60° C., 65° C. and 70° C., respectively; lane 10 represented 85° C., at which temperature the low mobility (reagent complex) band was no longer present. From lanes 7-9 progressive increases in the proportion of label in the high mobility band and decreases in the proportion in the low mobility band were observed; no changes were seen in lanes 2-6 in comparison to lane 1. From a similar experiment with a hybrid between the perfectly matched 27 base oligomer (L1, Table 1) and M13mp9 clone II-16 DNA, a Tm of approximately 71° C. was determined.

The Tm for the oligomer with a single base mismatch (L2, Table 1) hybridized to nitrocellulose-immobilized probe was determined by exposing dot blots (cf. example 11) to increasing temperatures in 6X SSC+10X Denhardt's solution for 10 min and counting the supernatants by scintillation spectrometry. Such a determination yielded a Tm of 57°, and melting of the hybrid spanned at least 30° C. Hybrids formed in solution are therefore more stable and more thermodynamically homogeneous.

In still another experiment using the 27-mer with a single base mismatch (L2, Table 1), no competitor DNA or 12.5 ng of M13mp8 clone 20 DNA was mixed in solution with 25 ng of purified reagent complex in the presence of 2X SSC. Paired reaction samples were incubated for 10 minutes at either 45° C. or 60° C. and then electrophoresed on a 15% polyacrylamide gel. The gel was subsequently subjected to autoradiography. It was observed that oligomer was not released from the probe strand at either temperature in the absence of competitor, while its displacement by competitor DNA was accelerated at the temperature closer to its melting point (i.e., 60° C. in this example).

EXAMPLE 9

Effect of Mismatches on the Rate of Displacement from and Stability of Reagent Complex In an experiment similar to Example 8, a perfectly matched albumin 32-mer and a 32-mer with 2 mismatches (resulting in G-T mispairing) were end labeled with phosphorus-32 and annealed to an albumin M13 clone as in Example 4. The sequence of the first of these two labeled polynucleotides is:

(perfectly matched 32-mer: 3'end-CTACAAACGTTTTTGATAC-GACTCCGTTTCCT 5'end (L3). In the mismatched 32-mer (L4), both underlined deoxycytidines of L3 were replaced by deoxythymidine. The stability of the reagent complexes was determined by melting experiments similar to those of Example 8 for 1, 2 and 4 hours. The 32-mer without a mismatch was stable up to 50° C. for 2 hours while the 32-mer with two mismatches was stable only up to 40° C. for 2 hours.

Each of the reagent complexes was incubated with 100 ng of competing (2A/Hae III) M13-albumin DNA (see Example 4) in a 10 microliter volume for 5, 10, 20, 40, 80, and 120 minutes. The reaction temperatures studied were 40° C. for both and also 50° C. for the perferct match. The samples were analyzed by electrophoresis and autoradiography as described in Example 4. At 40° C. the rate of displacement from the two reagent complexes was nearly identical. However, at 50° C., displacement from the perfectly matched reagent complex was significantly more rapid than from either of the reagent complexes at 40° C. This more rapid displacement is most likely an effect of the higher temperature of hybridization allowable with the perfectly matched reagent complex, the higher temperature resulting in a more optimal rate of hybridization (See J. G. Wetmur and N. Davidson, *J. Mol. Biol.* 31, 349-370 (1968)).

EXAMPLE 10

Effect of 10% PEG 6000 on the Rate of Strand Displacement

A $32_p$-labeled piece of PBR322 DNA was annealed to an M13 clone containing a complementary region within cloned pBR322 DNA as described in Example 7. The reagent complex was mixed in hybridization buffer with either 10 or 100 ng of a circular or linearized DNA strand of the opposite sense as competitor DNA. The displacement was carred out at 80° C. for 5, 15, 30, or 60 minutes and in the presence or absence of 10% PEG 6000, a poly (ethylene oxide) of 6000 number average molecular weight. The results were analyzed by gel electrophoresis and autoradiography. The rate of displacement in the presence of 10% PEG 6000 was at least ten-fold greater at short times of incubation (e.g., 5 minutes)· than in the absence of PEG 6000. After 60 minutes of reaction, however, an unexpected result was observed. The displaced DNA band disappeared from the autoradiogram; and most radiolabeled material migrated to the top of the gel. The explanation appears to be some sort of aggregation effect based on subsequent control experiments.

EXAMPLE 11

The Effect of Poly(ethylene oxide) PEG 6000 Concentration on Displacement Rate

Reagent complexes with M13mp9 clone II-16 DNA (see Example 1) and the 32p-labeled 27-mer with a single base mismatch (L2, Table 1) were prepared and purified as described in Example 3. Sample reactions were performed at 60° C. for 1 hour in 10 $\mu$l volumes of 2X SSC containing 25 ng of purified reagent complex, 25 ng of M13mp8 clone 20 DNA (see Example 1) and various concentrations of the polymer PEG 6000. Reactions were subsequently terminated by placing them on ice and samples were immediately subjected to electrophoresis in a 5% (top) and 20% (bottom) stacked polyacrylamide gel as described in Example 2. The polyacrylamide gel was then autoradiographed and the proportion of label in the high mobility band (free oligomer) scored using densitometry of the autoradiogram (Table 7).

TABLE 7

| % (w/v) PEG 6000 | M13mp8 clone 20 Competitor DNA Present | % Total Counts in High Mobility Band (Free Oligomer) |
|---|---|---|
| 0 | − | 38 |
| 0 | + | 82 |
| 6 | − | 8 |
| 6 | + | 98 |
| 9 | − | 8 |
| 9 | + | 98 |
| 12 | − | 13 |
| 12 | + | 88 |
| 15 | − | 5 |
| 15 | + | 63 |

These data indicate that significant changes in the extent of oligomer displaced during competitive hybridizations can be achieved when PEG 6000 is included in reaction samples to a concentration in the range of 6-12%. Other experiments (data not shown; also see Example 10) suggest this increased extent of oligomer displacement is due to an increased rate of displacement from reagent complexes.

EXAMPLE 12

Displacement of Release Tag from Nitrocellulose-Bound Probe by Competitor DNA

Single-stranded M13mp9 clone II-16 DNA (see Example 1) was applied in dots (0.25 $\mu$g each) to nitrocellulose filters, baked two hours at 80° C. and hybridized to a 32p-end labeled 27-mer with a single base mismatch (L2, Table 1) at 50° C. in 6X SSC plus 10X Denhardt's solution overnight. After extensive washes in 6X SSC (each dot retaining approximately 25,000 cpm), the dots were placed individually in 1.25 ml reaction mixtures containing 6X SSC plus 10X Denhardt's solution and either no competitor DNA, 2 $\mu$g of M13mp8 clone 20 DNA (see Example 1), or 2 $\mu$g of M13mp8 DNA (non-homologous competitor. Samples of 100 $\mu$l were removed at intervals and counted by liquid scintillation spectrometry (Table 8 reports the results in counts per minutes in the 100 $\mu$l aliquots of the supernatant.

TABLE 8

| Displacement time | No Competitor DNA | Competitor M13mp8 clone 20 DNA | m13mp8 DNA |
|---|---|---|---|
| 40 min. | 40 (0) | 73 (33) | 41 (1) |
| 60 min. | 45 (5) | 108 (68) | 44 (4) |
| 125 min. | 56 (16) | 195 (155) | 59 (19) |
| 180 min. | 73 (33) | 320 (280) | 74 (34) |
| 250 min. | 94 (54) | 424 (384) | 92 (52) |
| 395 min. | 141 (101) | 652 (612) | 134 (94) |

Values in brackets represent the raw (unbracketed) data after subtracting the 40 cpm machine background. These data show that the sample target nucleotide sequence in M13mp8 clone 20 DNA specifically displaces the radiolabeled release tag oligomer while sample DNA containing no target nucleotide sequence (i.e., M13mp8 DNA) does not displace oligomer above background levels.

EXAMPLE 13

Use of a Reagent Complex Having a Residual Binding Region

A portion of plasmid pBR322 DNA located between the Eco RI and Sal I recognition sites was cloned into bacteriophage M13mp8 or M13mp11. A 32p-labeled 19 base primer complementary to sequences adjacent to the insert in one of the M13 vectors (designated mp8pBR because M13mp8 was the cloning vector) was hybridized to the insert DNA of that clone and extended in vitro with *E. coli* DNA polymerase. The resulting partial double-stranded DNA was digested with the restriction enzyme Bam Hl and the 316 base long labeled polynucleotide product was then purified by denaturing agarose gel elecrophoresis and hybridized to mp8pBR DNA. The resultant hybrids were purified away from unhybridized labeled polynucleotide by passage over two successive Sapharose CL-4B columns.

The competitor for the displacement reaction was the opposite strand of the Eco Rl-Sal I fragment cloned in bacteriophage M13mp11 (and therefore designated mp11pBR). This competitor DNA is fully complementary to the 275 bases of the probe which derive from the pBR322 DNA insert in the mp8pBR molecule. An additional 41 base pairs in the labeled polynucleotide are not complementary to the competitor DNA, since they derive from sequences in the M13 vector. Thus, this probe has a tail (Residual Binding Region) which cannot be displaced by the competitor DNA, but must be melted off after a portion of the labeled polynucleotide has been displaced from the probe.

Displacement of this labeled polynucleotide was shown to occur in two steps, and to require a high reaction temperature. The release tag probe complex was hybridized to a 10-fold excess of circular or partially digested competitor at 70° C. in 100 mM NaCl, 100 mM Tris, pH 8.0 for 2 hours. Aliquots of the reaction mix were then heated for 5 or 15 minutes at either 80° C., 85° C. or 90° C. The reactions were then quenched on ice and the samples were analyzed on an agarose gel by electrophoresis followed by autoradiography.

After incubation with circular competitor DNA at 70° C., more than 90% of the reagent complex had become associated with target nucleotide sequence as indicated by a shift in the mobility of the reagent complex on the gel. No such shift was seen when partially digested competitor DNA was used. Because the competitor DNA associates with the probe polynucleotide without displacing the labeled polynucleotide, hybridization of the competitor and reagent complex results in a detectable shift on the autoradiogram of labeled material towards a position of lower mobility. Raising the temperature to within the range of 80° C. to 90° C. for 5 or 15 minutes resulted in the displacement of labeled polynucleotide from the probe up to a maximum of 80% under the specified conditions.

An experiment similar to the above demonstrated that the observed displacement events were specific. Incubation of the same reagent complex described above with a 10-fold molar excess of non-specific competitor M13 mp7 DNA at 85° C. in 100 mM NaCl, 100 mM Tris, pH 7.5 for 2 hours resulted in no displacement above background levels of unbound labeled polynucleotide. The background is likely due to slight contamination of the reagent complex with unhybridized labeled polynucleotide. Incubation of this same reagent complex with an equimolar or 10-fold molar excess of the specific competitor mp11pBR at 85° C. under similar conditions again resulted in displacement of up to about 80% of the labeled polynucleotide from the probe.

EXAMPLE 14

Release Tag Displacement from a Probe Polynucleotide Tethered on a Solid Support Single-stranded DNA from an albumin-M13 clone (4A the probe of Example 4) was prepared and digested with the restriction enzyme Hae III to produce small linear DNA fragments containing human albumin cDNA sequences. The linearized DNA was then tailed with a mixture of nucleotides including a biotinylated derivative of dUTP as follows. The solution for the tailing reaction contained 200 mM potassium cacodylate, 1 mM 2-mercaptoethanol, 1 mM cobalt chloride, 0.05 mM dTTP, 0.05 mM dCTP, and 0.1 mM biotinylated dUTP. Four units of terminal deoxynucleotidyl transferase were added and the reaction mixture incubated for 1 hour at 37° C. Control reactions indicated that several hundred nucleotides were added to each DNA fragment although not all tails contained a biotinylated derivative (presumably due to a slower rate of incorporation of the biotinylated derivative). The tailed DNA was then annealed to 32p-labeled albumin 32-mer (oligomer L3 of Example 9) as described in Example 4. The annealing reaction mixture (reagent complex) was passed over an 0.4 ml packed volume of avidin-agarose (Sigma) in hybridization buffer (1M NaCl, 50 mM tris, pH 8.0, 5X Denhardt's solution. The flow-through was passed over the column again and the column was then washed extensively at room temperature with hybridization buffer. The avidin-agarose beads containing the hybrid were then removed from the column and distributed into 50 µl aliquots in Eppendorf microfuge tubes. There were approximately 30,000 cpm in each aliquot. Various amounts of specific competitor used in Example 4 (between 0 and 200 ng) were added to each microfuge tube and the samples were incubated at 50° C. for 2 hours. Following the reaction, the contents of the tubes were transferred into small disposable columns (Bio-Rad Dispo-columns). Following a brief centrifugation, the eluate solution was recovered in an Eppendorf microfuge tube and quantitated by Cerenkov counting. The eluted cpm were as follows:

TABLE 9

| Amount competitor DNA | Eluted cpm (% of input) |
| --- | --- |
| 0 | 343 (1.2%) |
| 0.5 | 454 |
| 2 | 553 |
| 10 | 1295 |
| 50 | 4822 |
| 100 | 8965 |
| 200 | 13190 (43%) |

The 0.5 ng sample corresponds to roughly $1 \times 10^8$ competitor DNA molecules detectable (111 cpm above background) in 2 hours. A dose response curve drawn from this experiment shows a high degree of linearity.

EXAMPLE 15

Effect of *E. coli* rec A Protein on Rate of Strand Displacement

An 840 base pair Eco Rl-Bgl II restriction fragment containing the first 262 codons of the human serum albumin gene was subcloned into the single-stranded phage vector M13mp9, generating the clone designated M13mp9-albumin. (See Lawn et al., *Nucleic Acid Research* 9: 6103–6114 (1981) for the DNA sequence of the human albumin gene). Also inserted into this vector was the Eco RI fragment containing the polylinker from M13mp7. This polylinker sequence, inserted adjacent to the albumin sequence at the Eco RI site, is capable of forming a double-stranded hairpin structure in the otherwise single-stranded molecule. Cleavage of such a molecule with the enzyme Bam HI results in a linear and full length single-stranded molecule. An end-labeled polynucleotide was kinased using $^{32}$P-γ-ATP prepared by hybridizing a 14 base long oligonucleotide (5' end-GATGLAcALAAGAG-3'end) to sequences within the albumin insert, and extending it in vitro using *E. coli* DNA polymerase. The resulting DNA molecules were then digested with Pvu II, which cuts once in the human albumin insert. The final labeled polynucleotide, a 175 base long labeled and single stranded molecule, was then purified on a denaturing agarose gel by electrophoresis. The purified labeled polynucleotide was hybridized to the above M13mp9-albumin strand which serves as the probe polynucleotide; the probe used was either circular or had been linearized with Bam HI. Unhybridized labeled polynucleotide was removed from the reagent complex by passage over two successive Sepharose ® CL-4B columns.

Model competitor DNAs used in displacement experiments were either the complementary DNA strand to the human albumin sequence of the M13mp9-albumin clone inserted in the M13 vector mp8 (and hereafter designated as M13mp8-albumin), or a denatured double-stranded 840 base pair Eco RI-Bgl II fragment which is colinear with the insert in the M13mp9-albumin clone. The displacement reactions were carried out by incubating approximately 10 nanograms of the reagent complex containing a circular or linear probe polynucleotide with 10 or 50 nanograms of competitor DNA. All reactions were done in solutions containing Tris, pH 7.5, 25 mM $MgCl_2$, bovine serum albumin, DTT and 8 mM ATP. Reactions containing either no *E. coli* rec A protein, 5 picomoles of rec A protein or 10 picomoles of rec A protein were incubated for 60 minutes at 37° C. The reactions were stopped and the DNA deproteinated by adding chemical reagents to raise the final sample solution concentration to 20 mM EDTA, 0.4% SDS and 0.4 mg/ml proteinase K and incubating at 37° C. for 30 minutes. The amount of displacement was assayed by separating the reagent complex from displaced strands on a 2% agarose gel by electrophoresis, and autoradiographing the gel overnight.

When a displacement reaction was done using reagent complex with a circular probe polynucleotide and M13mp8-albumin DNA but without the addition of rec A protein under the conditions described above, no detectable displacement of the release tag from the probe was observed. The addition of up to 10 pmol of rec A protein to the reaction between the circular probe polynucleotide-labeled polynucleotide complex and the circular single stranded competitor resulted in the displacement of approximately 5% of the probe. However, most of the reagent complex was shifted to a position of low mobility on the gel, indicating that rec A protein had promoted the association of the competitor DNA and the reagent complex. This suggested that topological constraints prevented the displacement reaction from going to completion. When the linearized probe polynucleotide-labeled polynucleotide complex was used, the addition of 10 picomoles of rec A protein resulted in a displacement of approximately 75% of the release tag from the probe using circular competitor DNA. Less displacement was observed when 5 pmol of rec A was used, and increasing the amount of the competitor DNA to a 5-fold molar excess resulted in no observable increase in displacement, suggesting that the action of rec A protein is limiting in this reaction. Displacement was also observed when the double-stranded linear 840 base pair fragment was denatured and used as competitor DNA in a similar experiment to the above. A 10-fold molar excess of this linear competitor resulted in the displacement of only about 10% of the labeled polynucleotide even the presence of rec A protein; increasing the competitor DNA concentration to a 40-fold molar excess resulted in displacement of up to 40% of the labeled polynucleotide. It is likely that this reaction was less efficient due to the reannealing of the two self-complementary strands of the competitor DNA which were in excess with respect to the reagent complex.

EXAMPLE 16

Effect of Competitor DNA Strand Size Using A Constant Size Target Binding Region A $^{32}P$-labeled 32-mer (L3 of Example 9) complementary to a portion of the human serum albumin gene was hybridized to an albumin-M13 clone containing 350 nucleotides of the albumin coding region, this clone was prepared in analogous fashion to the clone described in Example 4. Some of this reagent complex hybrid was digested with the restriction enzyme Hae III to linearize the probe and to create a smaller probe fragment to which was bound the labeled polynucleotide. A plasmid containing a human serum albumin sequence complementary to the albumin DNA insert of the above clone was digested with one of several restriction endonucleases to generate a number of fragments, at least one of which contained the complete complementary 350 nucleotide region but which in addition contained additional non-complementary sequences so that the total DNA fragment sizes containing the complementary albumin sequence were 350, 2800 bp 5900 bp base pairs (bases after subsequent denaturation). These fragments were used separately as competitor DNA in strand displacement reactions.

Displacement reactions were set up with each of the denatured competitor DNAs in equimolar amounts based on the fragment sizes containing the complementary albumin sequence. All samples were incubated at 50° C. for 15, 30, 60, or 120 minutes. Either linearized or circular probes were used in the reagent complexes. The size of the incoming competitor DNA strand had a significant effect on the release tag displacement rate from the linearized reagent complex, with the rate decreasing by a factor of 3 or 4 as the competitor DNA size increased from 350 to 5900 bases. With the circular probe polynucleotide in the reagent complex, there was also a significant effect of size of the competitor DNA strand. The overall rate of displacement from the circular reagent complex was slower than from the linear hybrid, probably due to effects of both the size and topology of the circular reagent complex.

What is claimed is:

1. A method for determining the presence of a predetermined target nucleotide sequence in the nucleic acid of a biological sample which comprises the steps:
   (a) providing a reagent complex of (i) a probe polynucleotide which is capable of base pair binding via hydrogen bonds of purine/pyrimidine bases to the target nucleotide sequence, and (ii) a labeled polynucleotide which is bound by base pair binding via hydrogen bonds of purine/pyrimidine base pairs to the probe polynucleotide of at least about 20 nucleotides in a region of the probe polynucleotide at least partially coextensive with the region in which the probe polynucleotide is capable of binding to the target nucleotide sequence;
   (b) contacting the reagent complex with a biological sample under conditions in which the target nucleotide sequence, if present in the biological sample, binds to the probe polynucleotide and displaces labeled polynucleotide from the complex; and
   (c) determining the presence of labeled polynucleotide displaced from the reagent complex.

2. The method of claim 1 wherein the region of the probe polynucleotide to which the labeled polynucleotide is bound by base pair binding is a labeled polynucleotide binding region of about 20 to about 1000 nucleotides in length.

3. The method of claim 1 wherein the probe polynucleotide contains a target binding region capable of base pair binding to the target nucleotide sequence and a labeled polynucleotide binding region bound to bases of the labeled polynucleotide in the complex, and wherein the labeled polynucleotide binding region is contained within the target binding region.

4. The method of claim 3 wherein the labeled polynucleotide binding region is adjacent to one end of the target binding region.

5. The method of claim 4 wherein the labeled polynucleotide binding region is about 20 to about 500 nucleotides in length.

6. The method of claim 5 wherein the portion of the target binding region that is not part of the labeled polynucleotide region is at least about 100 nucleotides in length, and is at least as large as the labeled polynucleotide binding region.

7. The method of claim 4 wherein the portion of the target binding region that is not part of the labeled polynucleotide region is at least about 15 nucleotides in length.

8. The method of claim 4 wherein an end of the target binding region of the probe is adjacent to a free end of the probe polynucleotide.

9. The method of claim 1 wherein the probe polynucleotide contains a target binding region capable of base pair binding to a sample target nucleotide sequence and contains a labeled polynucleotide binding region bound by purine/pyrimidine base pairing to the labeled polynucleotide of at least about 15 nucleotides; at least some of the nucleotides of the labeled polynucleotide region being included in the target binding region; and no more than about 15 nucleotides of the labeled polynucleotide binding region being outside the target binding region.

10. The method of claim 1 wherein the probe polynucleotide is immobilized to a solid support in the complex.

11. The method of claim 10 wherein the probe polynucleotide is covalently linked to the solid support in the complex.

12. The method of claim 10 wherein the determining step (c) comprises:
(c1) separating a first phase containing immobilized probe polynucleotide from a second phase comprising displaced labeled polynucleotide; and
(c2) determining the presence of labeled polynucleotide in the second phase.

13. The method of claim 10 wherein the probe polynucleotide contains a target binding region capable of base pair binding to the target nucleotide sequence and a labeled polynucleotide binding region bound by purine/pyrimidine base pairing to bases of the labeled polynucleotide in the complex, and wherein the labeled polynucleotide binding region is contained within the target binding region.

14. The method of claim 13 wherein the probe polynucleotide is attached to the solid substrate adjacent to one end of the probe polynucleotide and the target binding region is adjacent to the opposite end of the probe polynucleotide.

15. The method of claim 1 wherein the probe polynucleotide is DNA.

16. The method of claim 1 wherein the reagent complex is free in solution during the contacting step (b).

17. The method of claim 16 wherein the determining step (c) comprises:
(c1) separating the reagent complex remaining from a portion of the reaction solution after the contacting step (b), and
(c2) determining the presence of any displaced labeled polynucleotide in a solution phase after separation.

18. The method of claim 17 wherein the separating step (c1) comprises a chromatographic separation.

19. The method of claim 17 wherein the separating step (c1) comprises immobilizing the reagent complex to a solid substrate from which the liquid phase is separated and the amount of displaced labeled polynucleotide is determined in the liquid phase.

20. The method of claim 19 wherein the probe polynucleotide contains an affinity reagent and wherein the separating step (c) comprises immobilizing the reagent complex to the solid support by binding the affinity reagent.

21. The method of claim 20 wherein the affinity reagent is biotin.

22. The method of claim 1 wherein the labeled polynucleotide is a polynucleotide bonded to a moiety detectable by light emission or absorption.

23. The method of claim 1 wherein the labeled polynucleotide is radioactively labeled.

24. The method of claim 1 wherein the labeled polynucleotide is a polynucleotide bonded to an enzyme label.

25. The method of claim 1 wherein the labeled polynucleotide is a polynucleotide bonded to an affinity reagent and the determining step (c) includes contacting the displaced labeled polynucleotide with a detectable material containing the affinity complement of the affinity reagent.

26. The method of claim 25 wherein the affinity reagent is biotin.

27. The method of claim 1 wherein the target nucleotide sequence is DNA.

28. The method of claim 27 wherein the probe polynucleotide is DNA.

29. The method of claim 1 wherein the base pairing between the labeled polynucleotide and the probe polynucleotide is interrupted by at least one mismatched pair.

30. The method of claim 29 wherein said mismatched pair is between a naturally-occurring base and a chemically-modified base, and is of lesser binding affinity than between the naturally occurring base and its matched naturally-occurring complementary base.

31. The method of claim 1 wherein the target nucleotide sequence is RNA.

32. A diagnostic reagent for determining the presence of a predetermined target nucleotide sequence in the nucleic acid of a biological sample comprising:
(i) a probe polynucleotide which is capable of base pair binding via hydrogen bond of purine/pyrimidine base pairs to the target nucleotide sequence, and
(ii) a labeled polynucleotide which is bound by base pair binding via hydrogen bonds of purine/pyrimidine base pairs to the probe polynucleotide in a labeled polynucleotide binding region of the probe polynucleotide, the labeled polynucleotide binding region being of about 20 to about 1000 nucleotides in length and being at least partially coextensive with the region in which the probe polynucleotide is capable of base pair binding to the target nucleotide sequence;

the potential base pair binding between the target nucleotide sequence and the probe polynucleotide being capable of displacing the labeled polynucleotide from the reagent complex.

33. The diagnostic reagent of claim 32 wherein the probe polynucleotide contains a target binding region capable of base pair binding to the target nucleotide sequence and wherein the labeled polynucleotide binding region is contained within the target binding region.

34. The diagnostic reagent of claim 33 wherein the labeled polynucleotide binding region is adjacent to one end of the target binding region.

35. The diagnostic reagent of claim 32 wherein the portion of the target binding region that is not part of the labeled polynucleotide binding region is at least about 100 nucleotides in length.

36. The diagnostic reagent of claim 32 wherein the probe polynucleotide contains a target binding region capable of base pair binding to the target nucleotide sequence, at least some of the nucleotides of the labeled polynucleotide binding region being includes in the target binding region and no more than about 15 nucleotides of the labeled polynucleotide binding region being outside the target binding region.

37. The diagnostic reagent of claim 32 free in solution.

38. The diagnostic reagent of claim 32 wherein the base pairing between the labeled polynucleotide and the probe polynucleotide is interrupted by at least one mismatched pair.

39. The diagnostic reagent of claim 32 wherein the labeled polynucleotide is a polynucleotide bonded to a moiety detectable by light emission or absorption.

40. The diagnostic reagent of claim 32 wherein the labeled polynucleotide is a polynucleotide bonded to an enzyme label.

41. The diagnostic reagent of claim 32 wherein the labeled polynucleotide is radioactively labeled.

42. The diagnostic reagent of claim 32 wherein the labeled polynucleotide is a polynucleotide bonded to an affinity reagent label.

43. The diagnostic reagent of claim 42 wherein the affinity reagent is biotin.

44. A method for determining the presence of a predetermined target nucleotide sequence in the nucleic acid of a biological sample which comprises the steps:
  (a) providing a reagent complex of (i) a probe polynucleotide which is capable of base pair binding via hydrogen bonds of purine/pyrimidine bases to the target nucleotide sequence, and (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of binding to the target nucleotide sequence;
  (b) contacting the reagent complex with a biological sample under conditions in which the target nucleotide sequence, if present in the biological sample, binds to the probe polynucleotide and displaces labeled polynucleotide from the complex; and
  (c) determining the presence of labeled polynucleotide remaining in the reagent complex.

45. A diagnostic reagent for determining the presence of a predetermined target nucleotide sequence in the nucleic acid of a biological sample comprising:
  (i) a probe polynucleotide which is immobilized to a solid support and is capable of base pair binding via hydrogen bonds of purine/pyrimidine base pairs to the target nucleotide sequence, and
  (ii) a labeled polynucleotide which is bound by base pair binding via hydrogen bonds of purine/pyrimidine base pairs to the probe polynucleotide in a region of the probe polynucleotide of at least about 20 nucleotides at least partially coextensive with the region in which the probe polynucleotide is capable of base pair binding to the target nucleotide sequence;

the poential base pair binding between the target nucleotide sequence and the probe polynucleotide being capable of displacing the labeled polynucleotide from the reagent complex.

46. The diagnostic reagent of claim 45 wherein the probe polynucleotide contains a target binding region capable of base pair binding to the target nucleotide sequence and a labeled polynucleotide binding region bound by purine/pyrimide base pairing to bases of the labeled polynucleotide in the reagent complex, and wherein the labeled polynucleotide binding region is contained within the target binding region.

47. The diagnostic reagent of claim 46 wherein the probe polynucleotide is attached to the solid support adjacent to one end of the probe polynucleotide and the target binding region is adjacent to the opposite end of the probe polynucleotide.

48. A diagnostic reagent for determining the presence of a predetermined target nucleotide sequence in the nucleic acid of a biological sample comprising:
  (i) a probe polynucleotide which is capable of base pair binding via hydrogen bonds of purine/pyrimidine base pairs to the probe polynucleotide in a region of the probe polynucleotide of at least about 20 nucleotides to least partially coextensive with the region in which the probe polynucleotide is capable of base pair binding to the target nucleotide sequence;
  (ii) a labeled polynucleotide which is bound by base pair binding via hydrogen bonds of purine/pyrimidine base pairs to the probe polynucleotide in a region of the probe polynucleotide at least partially coextensive with the region in which the probe polynucleotide is capable of base pair binding to the target nucleotide sequence;

the poential base pair binding between the target nucleotide sequence and the probe polynucleotide being capable of displacing the labeled polynucleotide from the reagent complex;

the probe polynucleotide containing an attached moiety for affinity separation from displaced labeled polynucleotide.

49. The diagnostic reagent of claim 48 wherein the attached moiety is biotin.

* * * * *

UNITED STATES PATENT AND TRADEMARK OFFICE
CERTIFICATE OF CORRECTION

PATENT NO. : 4,766,062
DATED : August 23, 1988
INVENTOR(S) : Steven E. Diamond

It is certified that error appears in the above-identified patent and that said Letters Patent is hereby corrected as shown below:

ON THE TITLE PAGE

[*] The Notice should read:

--The portion of the term of this patent subsequent to August 23, 2005 has been disclaimed.--

Signed and Sealed this

Twenty-ninth Day of August, 1989

Attest:

DONALD J. QUIGG

*Attesting Officer*   *Commissioner of Patents and Trademarks*